(12) United States Patent  
Anderson et al.

(10) Patent No.: US 7,674,248 B2
(45) Date of Patent: Mar. 9, 2010

(54) MEDICAL SUCTION APPARATUS AND METHODS FOR DRAINING SAME

(75) Inventors: Barry G. Anderson, Sheboygan, WI (US); Joseph M. Hand, Sheboygan Falls, WI (US)

(73) Assignee: Bemis Manufacturing Company, Sheboygan Falls, WI (US)

( * ) Notice: Subject to any disclaimer, the term of this patent is extended or adjusted under 35 U.S.C. 154(b) by 732 days.

(21) Appl. No.: 10/752,652

(22) Filed: Jan. 7, 2004

(65) Prior Publication Data

US 2004/0143228 A1 Jul. 22, 2004

Related U.S. Application Data

(63) Continuation-in-part of application No. 10/657,432, filed on Sep. 8, 2003, now abandoned.

(51) Int. Cl.
*A61M 1/00* (2006.01)
(52) U.S. Cl. .................... 604/319; 604/326
(58) Field of Classification Search .......... 604/541, 604/317–326, 385.04–385.05, 385.25–385.28, 604/385.101
See application file for complete search history.

(56) References Cited

U.S. PATENT DOCUMENTS

| | | | |
|---|---|---|---|
| 1,421,325 A | 6/1922 | Walker et al. | |
| 1,693,885 A | 12/1928 | Butterworth | |
| 1,827,085 A | 10/1931 | Huff | |
| 2,004,027 A | 6/1935 | Baxter | |
| 2,009,400 A | 7/1935 | Hapgood | |
| 2,073,746 A | 3/1937 | Keller | |
| 2,208,028 A | 7/1940 | Harrington | |
| 2,438,769 A | 3/1948 | Thomas | |
| 2,641,270 A | 6/1953 | Allen | |
| 2,799,301 A | 7/1957 | Ballard | |
| 2,886,071 A | 5/1959 | Rasmussen | |
| 3,171,447 A | 3/1965 | Fowler et al. | |
| 3,363,627 A | 1/1968 | Bidwell et al. | |
| 3,394,831 A | 7/1968 | Bathish et al. | |
| 3,482,583 A | 12/1969 | Fenn | |

(Continued)

FOREIGN PATENT DOCUMENTS

EP 0596132 A1 5/1994

(Continued)

OTHER PUBLICATIONS

Med Inc., Medical & Environmental Design, Inc.; Promotional Product Material, Jan. 15, 1991.

*Primary Examiner*—Tatyana Zalukaeva
*Assistant Examiner*—Lynne Anderson
(74) *Attorney, Agent, or Firm*—Michael Best & Friedrich LLP

(57) ABSTRACT

A drainage device and a method for draining a liner-type suction canister. The drainage device includes a swingarm, a drainhead, and a suction source. The drainhead is positioned to be in fluid communication with the liner-type suction canister. The swingarm rotates to activate the suction source and invert the liner-type suction canister. The contents of the liner-type suction canister drain to a sewer system. The method includes the acts of placing the liner-type suction canister on the swingarm, coupling the drainhead to the liner-type suction canister, rotating the swingarm, and activating the suction source.

21 Claims, 17 Drawing Sheets

U.S. PATENT DOCUMENTS

| | | |
|---|---|---|
| 3,556,101 A | 1/1971 | Economou |
| 3,603,328 A | 9/1971 | Fenn |
| 3,646,935 A | 3/1972 | Holbrook et al. |
| 3,671,982 A | 6/1972 | Sayles |
| 3,680,560 A | 8/1972 | Pannier, Jr. et al. |
| 3,685,517 A | 8/1972 | Reynolds et al. |
| 3,699,964 A | 10/1972 | Ericson |
| 3,719,197 A | 3/1973 | Pannier, Jr. et al. |
| 3,768,478 A | 10/1973 | Fertik et al. |
| 3,780,757 A | 12/1973 | Jordan |
| 3,782,414 A | 1/1974 | Holbrook |
| 3,791,394 A | 2/1974 | Hammelmann |
| 3,863,664 A | 2/1975 | Holbrook et al. |
| 3,866,608 A | 2/1975 | Reynolds et al. |
| 3,881,486 A | 5/1975 | Fenton |
| 3,897,599 A | 8/1975 | Artzer |
| 3,916,924 A | 11/1975 | McGowan |
| 3,945,392 A | 3/1976 | Deaton et al. |
| 3,958,730 A | 5/1976 | Caldwell |
| 3,989,046 A | 11/1976 | Pannier, Jr. et al. |
| 3,995,333 A | 12/1976 | Stephens |
| 4,004,590 A | 1/1977 | Muriot |
| 4,015,603 A | 4/1977 | Kurtz et al. |
| 4,049,555 A | 9/1977 | Matherne |
| 4,053,284 A | 10/1977 | Posch |
| 4,058,412 A | 11/1977 | Knapp et al. |
| 4,084,723 A | 4/1978 | Parker |
| 4,090,635 A | 5/1978 | Nelson et al. |
| 4,108,336 A | 8/1978 | Anderson, Jr. |
| 4,112,948 A | 9/1978 | Kurtz et al. |
| 4,135,515 A | 1/1979 | Muriot |
| 4,157,718 A | 6/1979 | Baehr |
| 4,195,633 A | 4/1980 | Nehring et al. |
| 4,195,672 A | 4/1980 | Freeman |
| 4,228,798 A | 10/1980 | Deaton |
| 4,238,892 A | 12/1980 | Geiss |
| 4,245,637 A | 1/1981 | Nichols |
| 4,258,824 A | 3/1981 | Kurtz et al. |
| 4,275,732 A | 6/1981 | Gereg |
| 4,306,557 A | 12/1981 | North |
| 4,321,922 A | 3/1982 | Deaton |
| 4,341,568 A | 7/1982 | Christensen |
| 4,345,342 A | 8/1982 | Saito |
| 4,356,084 A | 10/1982 | Hatton et al. |
| 4,363,340 A | 12/1982 | Naftulin |
| 4,384,580 A | 5/1983 | Leviton |
| 4,388,922 A | 6/1983 | Telang |
| 4,429,803 A | 2/1984 | Butterfield |
| 4,430,084 A | 2/1984 | Deaton |
| 4,430,085 A | 2/1984 | Ahrens |
| 4,455,140 A | 6/1984 | Joslin |
| 4,484,920 A | 11/1984 | Kaufman et al. |
| 4,519,427 A | 5/1985 | Ono et al. |
| 4,540,413 A | 9/1985 | Russo |
| 4,559,664 A | 12/1985 | Bohme et al. |
| 4,586,549 A | 5/1986 | White |
| 4,629,159 A | 12/1986 | Wellenstam |
| 4,631,050 A | 12/1986 | Reed et al. |
| 4,666,063 A | 5/1987 | Holoubek et al. |
| 4,673,006 A | 6/1987 | Speck |
| 4,676,281 A | 6/1987 | Nord |
| 4,676,287 A | 6/1987 | Fitzwater |
| 4,681,571 A | 7/1987 | Nehring |
| 4,685,480 A | 8/1987 | Eck |
| 4,698,060 A | 10/1987 | D'Antonio et al. |
| 4,704,106 A | 11/1987 | Shave et al. |
| 4,715,855 A | 12/1987 | D'Antonio et al. |
| 4,735,610 A | 4/1988 | Akkas et al. |
| 4,740,202 A | 4/1988 | Stacey et al. |
| 4,749,010 A | 6/1988 | Petell |
| 4,762,241 A | 8/1988 | Lang |
| 4,770,787 A | 9/1988 | Heath et al. |
| 4,781,707 A | 11/1988 | Boehringer et al. |
| 4,785,963 A | 11/1988 | Magley |
| 4,795,428 A | 1/1989 | Hwang |
| 4,795,448 A | 1/1989 | Stacey et al. |
| 4,808,159 A | 2/1989 | Wilson et al. |
| 4,809,860 A | 3/1989 | Allen |
| 4,813,563 A | 3/1989 | Ogden et al. |
| 4,820,351 A | 4/1989 | Hambleton et al. |
| 4,857,063 A | 8/1989 | Glenn |
| 4,863,446 A | 9/1989 | Parker |
| 4,867,738 A | 9/1989 | Mintz |
| 4,870,975 A | 10/1989 | Cronk et al. |
| 4,889,531 A | 12/1989 | D'Antonio et al. |
| 4,902,284 A | 2/1990 | D'Antonio et al. |
| 4,905,325 A | 3/1990 | Colditz |
| 4,913,179 A | 4/1990 | Engel et al. |
| 4,913,197 A | 4/1990 | Friedrich |
| 4,926,915 A | 5/1990 | Deussen et al. |
| 4,955,874 A | 9/1990 | Farrar et al. |
| 4,957,491 A | 9/1990 | Parker |
| 4,961,440 A | 10/1990 | Wright |
| 4,967,814 A | 11/1990 | Day, Jr. |
| 4,969,491 A | 11/1990 | Kiplinger |
| 4,972,976 A | 11/1990 | Romero |
| 5,011,470 A | 4/1991 | Kurtz et al. |
| 5,024,613 A | 6/1991 | Vasconcellos et al. |
| 5,026,358 A | 6/1991 | Everett, Jr. et al. |
| 5,027,872 A | 7/1991 | Taylor et al. |
| 5,033,492 A | 7/1991 | Mertens et al. |
| 5,045,077 A | 9/1991 | Blake, III |
| 5,049,273 A | 9/1991 | Knox |
| 5,053,026 A | 10/1991 | Andersen et al. |
| 5,064,101 A | 11/1991 | Richter et al. |
| 5,067,950 A | 11/1991 | Broadnax, Jr. |
| 5,071,035 A | 12/1991 | Kiplinger |
| 5,078,677 A | 1/1992 | Gentelia et al. |
| 5,119,830 A | 6/1992 | Davis |
| 5,121,778 A | 6/1992 | Baker et al. |
| 5,154,712 A | 10/1992 | Herweck et al. |
| 5,185,007 A | 2/1993 | Middaugh et al. |
| 5,186,195 A | 2/1993 | Wall |
| 5,192,439 A | 3/1993 | Roth et al. |
| 5,195,994 A | 3/1993 | Dieringer |
| 5,217,038 A | 6/1993 | Pinder |
| 5,222,530 A | 6/1993 | Baker et al. |
| 5,242,434 A | 9/1993 | Terry |
| 5,273,083 A | 12/1993 | Burrows |
| 5,300,050 A | 4/1994 | Everett, Jr. et al. |
| 5,349,995 A | 9/1994 | Perez |
| 5,351,859 A | 10/1994 | Jansen |
| 5,380,289 A | 1/1995 | Hemstreet et al. |
| 5,380,314 A | 1/1995 | Herweck et al. |
| 5,437,836 A | 8/1995 | Yamada |
| 5,439,460 A | 8/1995 | Hoover |
| 5,460,193 A | 10/1995 | Levallois et al. |
| 5,470,324 A | 11/1995 | Cook et al. |
| 5,546,979 A | 8/1996 | Clark, II et al. |
| 5,599,331 A | 2/1997 | Hemstreet et al. |
| 5,620,428 A | 4/1997 | Hand |
| 5,624,417 A | 4/1997 | Cook et al. |
| 5,637,103 A | 6/1997 | Kerwin et al. |
| 5,669,892 A | 9/1997 | Keogh et al. |
| 5,678,564 A | 10/1997 | Lawrence et al. |
| 5,683,371 A | 11/1997 | Hand |
| 5,688,255 A | 11/1997 | Hand |
| 5,725,516 A | 3/1998 | Cook et al. |
| 5,741,237 A | 4/1998 | Walker |
| 5,776,118 A | 7/1998 | Seifert et al. |
| 5,776,260 A | 7/1998 | Dunn et al. |
| 5,807,359 A | 9/1998 | Bemis et al. |
| 5,837,103 A | 11/1998 | Trokhan et al. |
| 5,871,476 A | 2/1999 | Hand |

| | | | | | | |
|---|---|---|---|---|---|---|
| 5,901,717 | A | 5/1999 | Dunn et al. | 6,358,232 B1 | 3/2002 | Hand et al. |
| 5,931,822 | A | 8/1999 | Bemis et al. | 6,368,310 B1 | 4/2002 | Bemis et al. |
| 6,027,490 | A | 2/2000 | Radford et al. | | | |
| 6,152,902 | A | 11/2000 | Christian et al. | | | |
| 6,244,311 | B1 | 6/2001 | Hand et al. | WO | 8623430 | 4/1986 |

FOREIGN PATENT DOCUMENTS

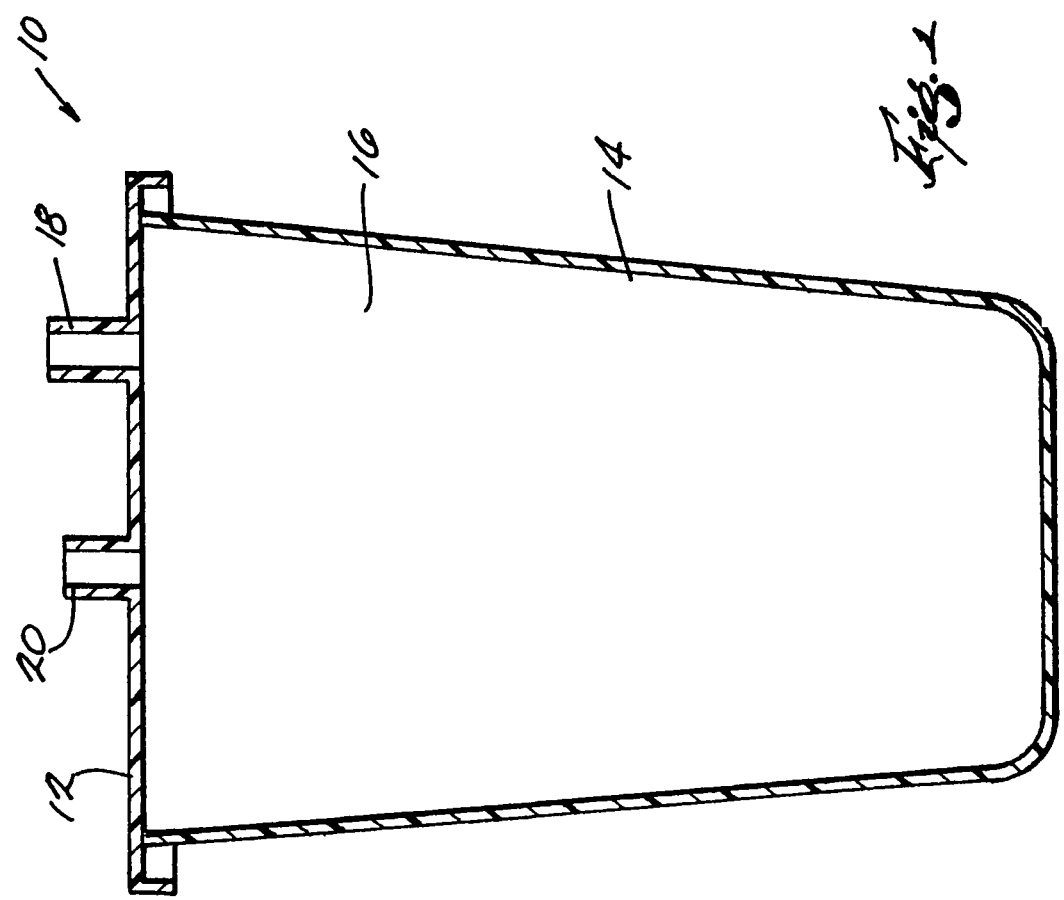

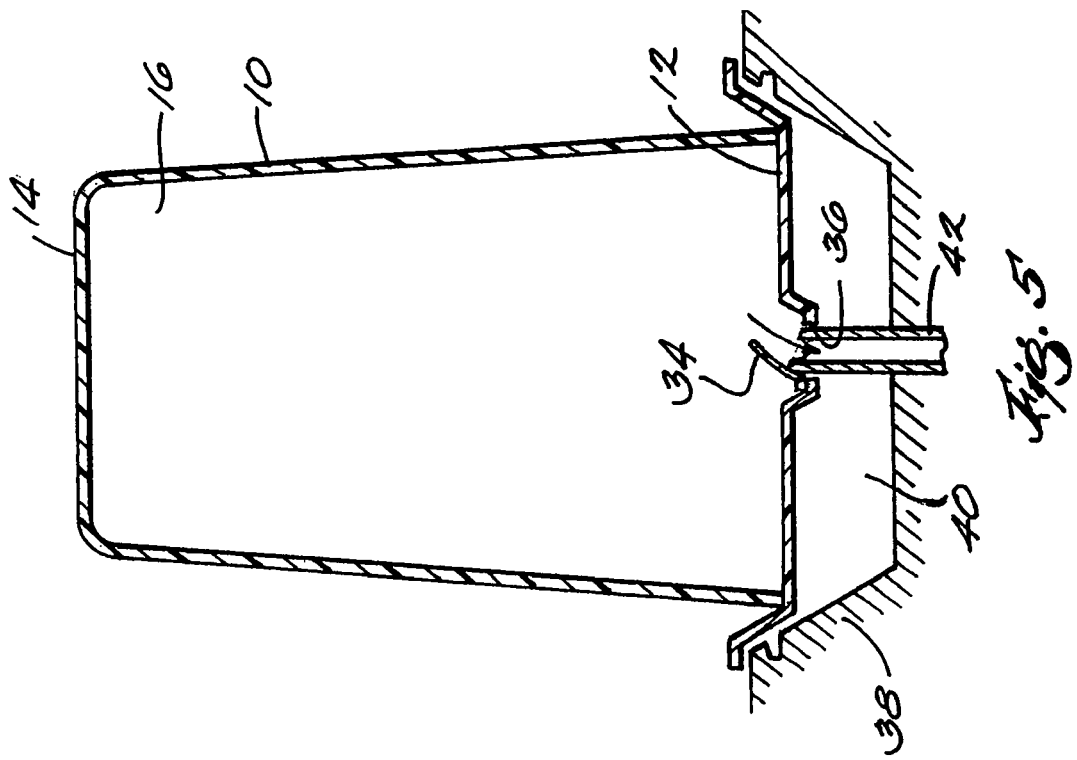
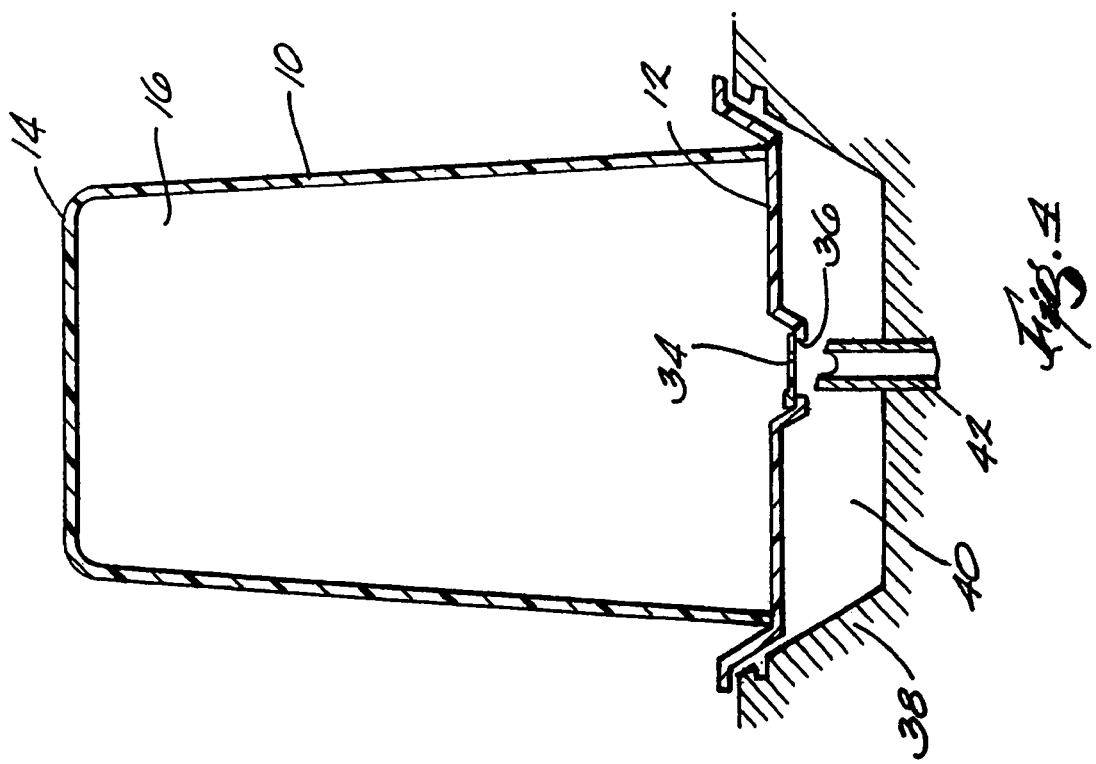

MEDICAL SUCTION APPARATUS AND METHODS FOR DRAINING SAME

RELATED APPLICATIONS

This patent application is a continuation-in-part of application Ser. No. 10/657,432, filed Sep. 8, 2003, now abandoned which claimed the benefit of prior application Ser. No. 09/819,243, filed on Mar. 28, 2001, now U.S. Pat. No. 6,626,877, which claimed the benefit of provisional patent Application No. 60/192,751, filed on Mar. 28, 2000.

BACKGROUND OF THE INVENTION

The invention relates to draining bodily fluid contained in the liner of a liner-type medical suction apparatus.

Medical suction systems are used in hospital environments and particularly during various surgical procedures to drain and store bodily fluid from a patient. In general, medical suction systems are used in conjunction with a vacuum source which enables the bodily fluid to be drained from the patient.

One type of medical suction system used to drain and contain fluid from a patient is an apparatus including a disposable bag-like liner and a cover secured to the liner. Such liners are thin-walled pliable plastic members. The cover typically includes a patient port for receiving the fluid from a patient and a vacuum port for establishing a vacuum within the liner. The vacuum draws fluid from the patient through the patient port for collection in the liner.

It has become important in environments such as hospitals to eliminate the handling of and thus reduce personnel exposure to bodily fluids. Hospitals typically dispose of the bodily fluid contained in a liner-type medical suction apparatus in various ways. Bodily fluid can be poured from the liner through a port in the cover down the hospital sink and into the sewer system, can be incinerated as a liquid or solid, or can be disposed of at an approved hazardous waste site. Since the liner is in the form of a pliable bag filled with liquid, special disposal handling is required in order to prevent puncturing or bursting due to contact with sharp objects.

SUMMARY OF THE INVENTION

The invention provides methods and apparatus for removing body fluids from a liner-type medical suction apparatus to eliminate the potential for a person handling the apparatus to come into contact with the fluid.

Specifically, the invention provides for methods of draining bodily fluid from a liner that is drained of potentially hazardous fluid without contact with the fluid. The liner is drained in conjunction with a drainage device. Various types of drainage devices can be employed to drain the liner.

More particularly, the invention provides a method for draining a liner-type medical suction apparatus, the liner-type medical suction apparatus including a liner, a liner interior filled with fluid, a cover, and a port in the cover. The method includes providing a drainage device, the drainage device including a conduit and a cradle. The method also includes positioning the cover of the liner-type medical suction apparatus within the cradle of the drainage device with the liner-type suction apparatus inverted, causing the conduit to communicate with the liner interior through the port, and draining the fluid from the liner interior through the conduit.

The invention provides a method for draining a liner-type medical suction apparatus, the liner-type medical suction apparatus including a liner, a liner interior filled with fluid, a cover, and a port in the cover. The method includes providing a drainage device, the drainage device including a movable support member and a conduit. The method also includes positioning the liner-type medical suction apparatus in a substantially upright position within the support member, attaching the conduit to the port, and moving the support member to cause the liner-type medical suction apparatus to move from the substantially upright position to a position in which the fluid flows out of the liner interior into the conduit.

The invention provides a medical apparatus including a liner-type medical suction apparatus. The liner-type medical suction apparatus includes a liner, a liner interior for containing fluid, a cover, a port in the cover, and a pre-attached tube coupled to the port and extending into the liner interior. The medical apparatus includes a drainage device including a housing. The medical apparatus also includes a conduit including a first end coupled to the drainage device housing and a second end coupleable to the port so that fluid in the liner interior can flow through the pre-attached tube and the conduit to the drainage device.

The invention provides a device for draining a liner-type medical suction apparatus, the liner-type medical suction apparatus including a liner, a liner interior filled with fluid, a cover, and a port in the cover. The device includes a drainage device housing and a cradle coupled to the drainage device housing, the cradle being adapted to support the cover of the liner-type medical suction apparatus when the liner-type medical suction apparatus is in an inverted position. The device also includes a breakout pipe including a first end coupled to the cradle and a second end for communication with the liner interior. The breakout pipe is movable upwardly between a storage position in which the second end is stored substantially within the cradle and a drainage position in which the second end is in communication with the liner interior through the cover.

The invention provides a device for draining a liner-type medical suction apparatus, the liner-type medical suction apparatus including a liner, a liner interior, a cover, and a port in the cover. The device includes a drainage device housing, a drain coupled to the drainage device housing, and a conduit including a first end coupled to the drain and a second end adapted for attachment to the port. The device also includes a support member coupled to the drainage device housing and adapted to support the liner-type medical suction apparatus. The support member is movable between a loading position in which the liner-type medical suction apparatus is in a substantially upright position and a drainage position in which the liner-type medical suction apparatus is in a position in which the fluid flows through the conduit to the drain.

The invention provides a device for draining a liner-type suction canister having a cover and a liner coupled to the cover, the cover having therein a port, the liner containing fluid to be drained. The device comprises a housing, a swingarm, a drainhead, a support member, and a suction source. The housing is in communication with a sanitary sewer line. The swingarm is coupled to the housing and movable between a first position and a second position. The drainhead includes a passageway and is moveable between a first position not engageable with the liner-type suction canister and a second position engageable with the liner-type suction canister, and in the second position, the passageway is adapted to be in fluid communication with the port in the cover of the liner-type suction canister. The support member is on the swingarm for supporting the liner-type suction canister. The suction source is in communication with the passageway and is adapted to drain the fluid contained in the liner-type suction canister from the liner through the drainhead to the sanitary sewer.

The invention provides a device for draining fluid contained in a liner-type suction canister. The device comprises a swingarm and a drainhead. The swingarm has thereon a support member adapted to support the liner-type suction canister, and is moveable between a first and a second position. The drainhead has a passageway therein, and is moveable between a first and a second position. The drainhead is adapted to engage the liner-type suction canister to enable fluid communication between the passageway and the fluid contained in the liner-type suction canister when the drainhead is in the second position.

The invention provides a device for draining fluid contained in a liner-type suction canister having a cover. The device comprises a housing and a swingarm. The swingarm is coupled to the housing, and is movable between a first position and a second position. The swingarm includes a support member adapted to support the liner-type suction canister and a drainhead having therein a passageway, the drainhead adapted to engage the cover of the liner-type suction canister to permit fluid to drain from the liner-type suction canister through the drainhead to the housing.

The invention provides a method for draining a liner-type suction canister filled with fluid. The method comprises the acts of placing the liner-type suction canister on a swingarm of a drainage device, coupling together a drainhead on the drainage device and the liner-type suction canister, rotating the swingarm with the liner-type suction canister thereon, and activating a suction source to drain the fluid from the liner-type suction canister through the drainhead.

The invention provides a method for draining a liner-type suction canister filled with fluid. The method comprises the acts of placing the liner-type suction canister on a swingarm of a drainage device, connecting a drainhead on the drainage device with the liner-type suction canister so as to establish fluid communication between the drainhead and a port on the liner-type suction canister, rotating the swingarm with the liner-type suction canister thereon, and activating a suction source to drain the fluid from the liner-type suction canister through the drainhead.

The invention provides a method for draining a liner-type suction canister filled with fluid. The method comprises the acts of placing the liner-type suction canister on a swingarm of a drainage device when the swingarm is in a first position, preventing movement of the swingarm, moving a drainhead on the drainage device from a first position to a second position in fluid communication with a port on the liner-type suction canister, securing the drainhead in the second position, enabling movement of the swingarm, rotating the swingarm from its first position to a second position, and activating a suction source to drain the fluid from the liner-type suction canister, through the drainhead, and to a sanitary sewer.

BRIEF DESCRIPTION OF THE DRAWINGS

FIG. 1 is a front view of a liner-type medical suction apparatus.

FIGS. 4 and 5 are sectional views of the apparatus and a third method for draining the liner.

Figure 3:
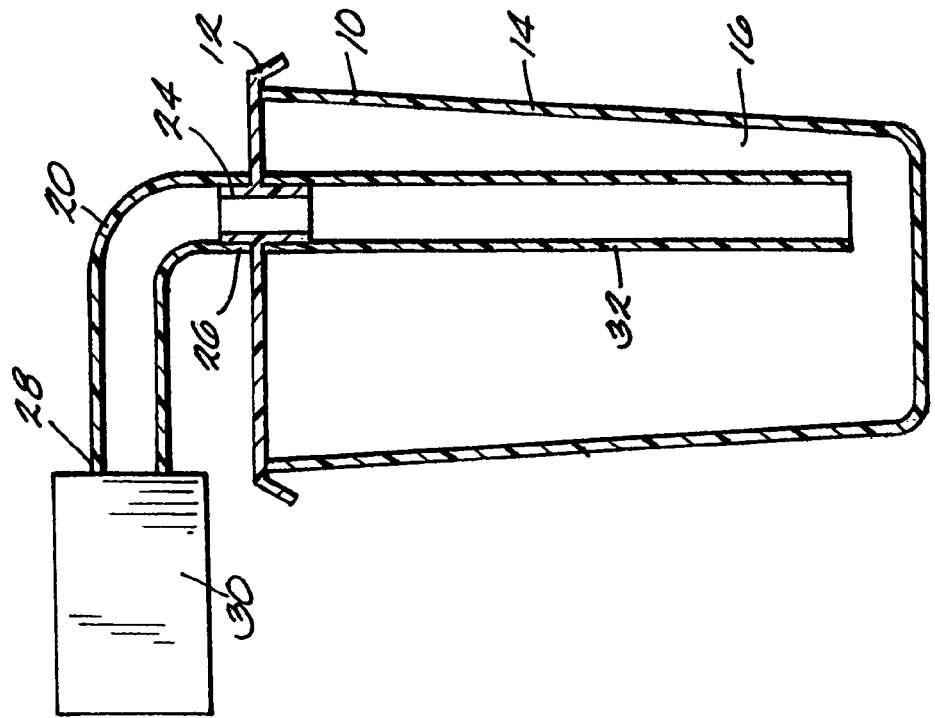
FIG. 3 is a sectional view of the apparatus and a second method for draining the liner.

Before one embodiment of the invention is explained in detail, it is to be understood that the invention is not limited in its application to the details of construction and the arrangement of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

DETAILED DESCRIPTION OF THE INVENTION

The entire disclosures of the prior filed applications referenced in the Related Applications section are incorporated herein by reference.

With reference to FIG. 1, there is shown a liner-type medical suction apparatus 10. The apparatus 10 includes a cover 12 and a liner 14 suitably attached to the cover 12. The liner 14 is a thin-walled bag having an interior 16 adapted to hold the fluid drained from a patient. The liner 14 is preferably fabricated from a plastic such as ultra low density polyethylene, however, other materials can be used as desired.

The cover 12 includes a patient port 18, a suction port 20, and other access ports as desired. A patient conduit is connectable to the patient port 18 to enable communication between the patient and the interior 16 of the liner 14. A suction conduit is connectable to the suction port 20 to enable communication between the interior 16 of the liner 14 and a suction source, such as a hospital suction system.

To drain fluid from a patient, the patient and suction conduits are respectively secured to the patient and suction ports 18 and 20. The liner 14 is supported by a stand or by a rigid outer container or canister (not shown), and fluid is drained from a patient as is conventionally known.

When it is desired to drain the fluid contained in the liner 14, one of the seven methods described herein can be employed to drain the fluid contents from the interior 16 of the liner 14 while eliminating any contact with the fluid by the person handling the apparatus 10.

Figure 2:
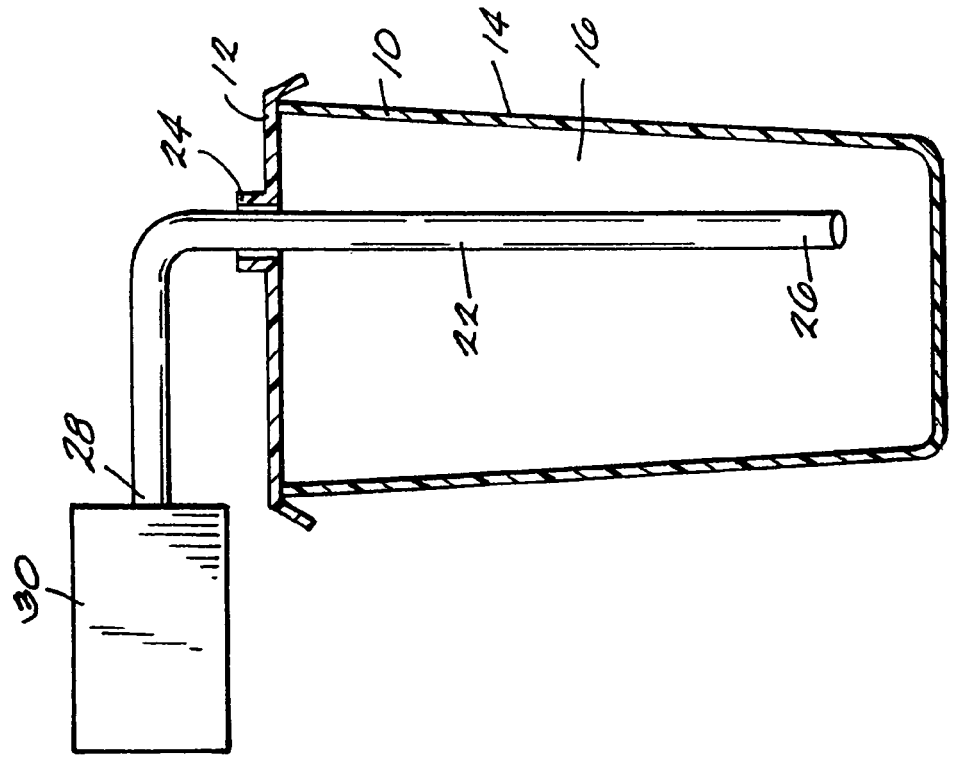
FIG. 2 is a sectional view of the apparatus and one method for draining the liner.

Turning now to FIG. 2, there is shown the liner-type medical suction apparatus 10. To drain the fluid contents of the interior 16 of the liner 14, a conduit 22 is positioned in the interior 16 of the liner 14, such as through an open port 24 in the cover 12. One end 26 of the conduit 22 is positioned in the interior 16 of the liner 14 and the other end 28 is in communication with a drainage device 30 which evacuates the fluid from the interior 16 of the liner 14. To support the apparatus during drainage, the apparatus 10 can be hung from a stand or hung from a bracket secured to a wall.

With reference to FIG. 3, a second method for draining the apparatus 10 is shown. In this embodiment, a tube 32 is pre-attached to the inside of the cover 12 and hangs down into the interior 16 of the liner 14. To drain the liner 14, the end 26 of the conduit 22 is secured to the open port 24 on the cover 12 and the second end 28 is secured to the drainage device 30, such as was described above.

Turning now to FIGS. 4 and 5, a third method for draining the liner 14 is shown. With this method, the cover 12 includes a flapper-style valve 34 positioned in a port 36. To drain the fluid from the liner 14, the apparatus 10 is inverted with respect to a drainage device 38 and the cover 12 is positioned in a cradle 40 of the drainage device 38. Preferably, the drainage device 38 creates a negative pressure or suction force within the cradle 40 to hold the apparatus 10 in place. The drainage device 38 includes a breakout pipe 42 that is movable vertically. After the cover 12 has been positioned in the cradle 40, the pipe 42 is actuated such that it moves upwardly toward the valve 34. Further upward movement of the pipe 42 pivots the valve 34 to enable fluid to escape the liner 14 through the pipe 42 as is shown by the arrow in FIG. 5. After drainage, the pipe 42 is actuated downwardly, the valve 34 returns to its normally closed position and the apparatus 10 can be removed from the cradle 40. One suitable construction for the pipe 42 is disclosed in U.S. patent application Ser. No. 09/239,842, titled "Method and Apparatus for Removing and Disposing of Body Fluids," filed Jan. 29, 1999, the entire contents of which is incorporated herein by reference.

Figure 6:
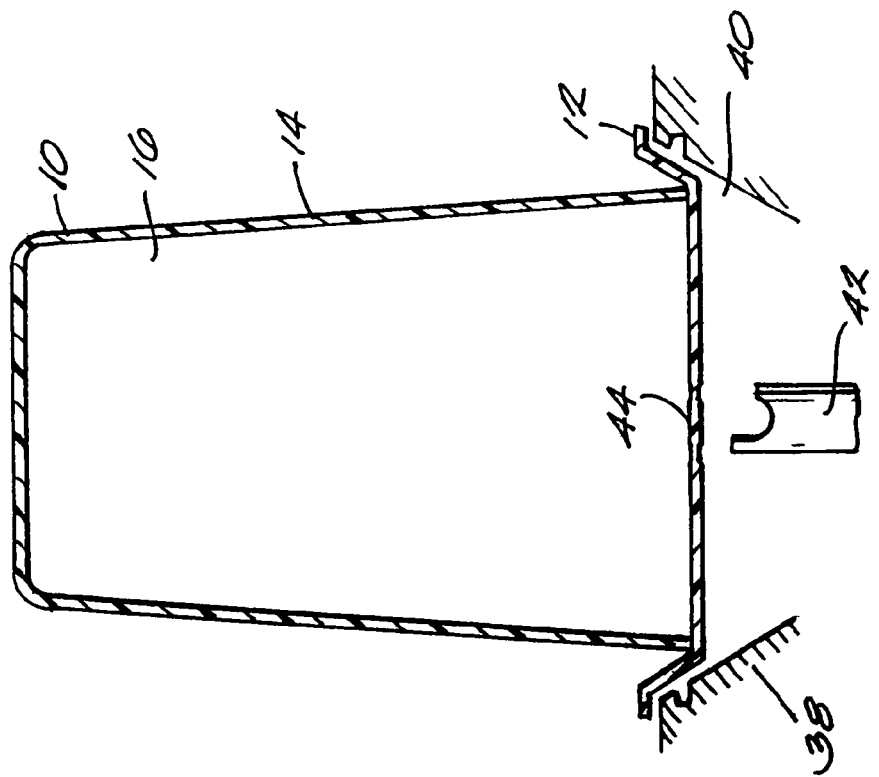
FIG. 6 is a sectional view of the apparatus and a fourth method for draining the liner.

A fourth method for draining the liner is shown in FIG. 6. In this embodiment, the cover 12 includes a breakaway portion 44. Preferably, the breakaway portion 44 is a frangible part of the cover 12. To drain the fluid from the liner 14, the apparatus 10 is inverted with respect to the drainage device 38, the cover 12 is positioned in the cradle 40, and drainage device 38 creates a suction force within the cradle 40 to hold the apparatus 10 in place. After the cover 12 has been positioned in the cradle 40, the pipe 42 is actuated upwardly toward the portion 44. Further upward movement of the pipe 42 breaks the breakaway portion 44 allowing fluid to drain from the interior 16 of the liner 14 through the pipe 42. After drainage, the pipe 42 is actuated downwardly and the apparatus 10 can be removed from the cradle 40.

Figure 7:
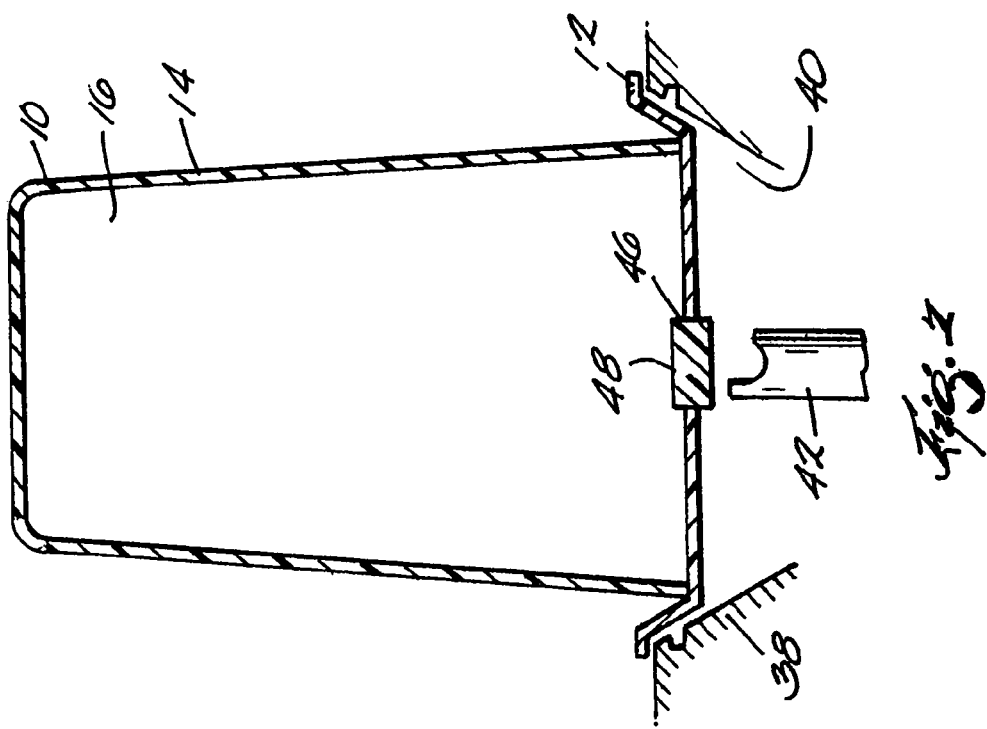
FIG. 7 is a sectional view of the apparatus and a fifth method for draining the liner.

As shown in FIG. 7, a fifth method is depicted for draining the liner 14. In this method, the cover 12 includes a port 46 that is normally occluded with a plug 48. To drain the fluid from the liner 14, the apparatus 10 is inverted with respect to the drainage device 38, the cover 12 is positioned in the cradle 40, and the drainage device 38 creates a suction force within the cradle 40 to hold the apparatus 10 in place. After the cover 12 has been positioned in the cradle 40, the pipe 42 is actuated upwardly toward the plug 48. Further upward movement of the pipe 42 dislodges the plug 48 from the port 46 allowing fluid to drain from the interior 16 of the liner 14 through the pipe 42. After drainage, the pipe 42 is actuated downwardly and the apparatus 10 can be removed from the cradle 40.

Figure 8:
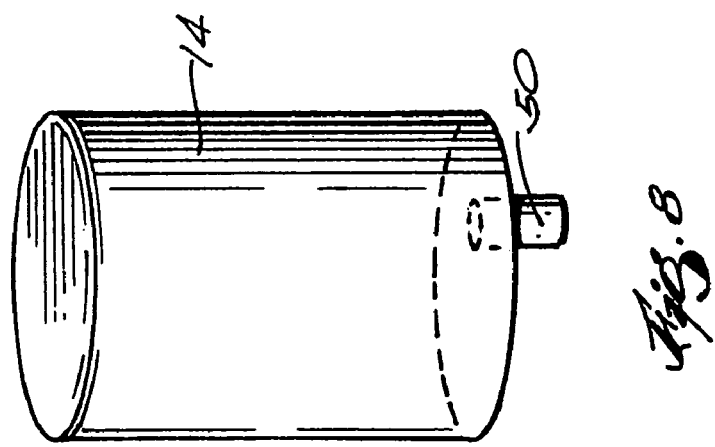
FIG. 8 is a perspective view of a liner and sixth method for draining the liner.

Turning now to FIG. 8, a sixth method is shown for draining the liner 14. In this embodiment, the liner 14 includes a nipple portion 50 on the bottom of the liner 14. To drain the contents of the liner 14, the nipple portion 50 is severed or punctured allowing fluid to drain from the interior 16 of the liner 14.

In addition to the cover structures shown in FIGS. 4-8, other cover structures may be employed. While the structures disclosed in U.S. patent application Ser. No. 09/239,842 are generally shown as being incorporated into the bottom of a medical suction apparatus, those structures may also be incorporated into the cover of a liner-type medical suction apparatus.

Figure 9:
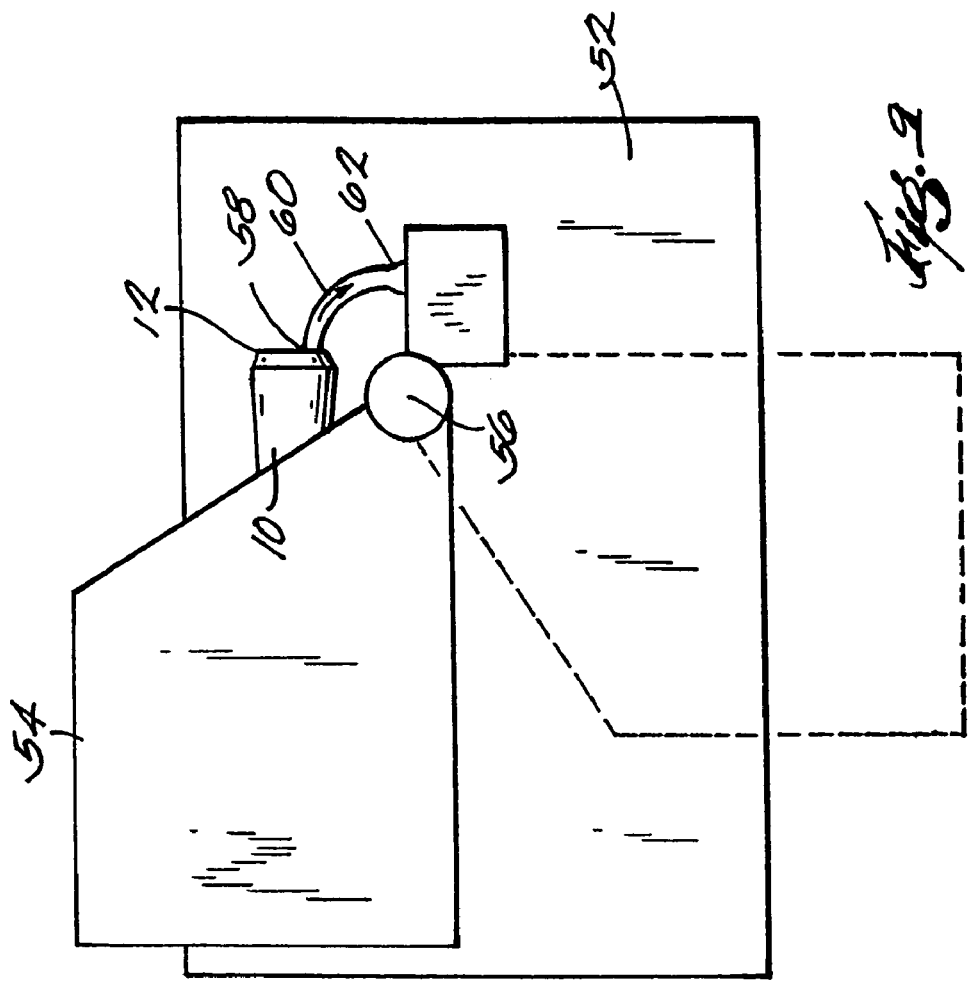
FIG. 9 is a front view of a seventh method for draining the liner.

With reference to FIG. 9, a seventh method for draining the liner 14 is shown. In this embodiment, a drainage device 52 includes a pivotable swing arm 54 that rotates about a pivot point 56. To drain the liner 14, the apparatus 10 is positioned in the swing arm 54 with the swing arm 54 in a first position, shown in phantom in FIG. 9. One end 58 of a conduit 60 is secured to a port on the cover 12 and the second end 62 of the conduit 60 is secured to the drainage device 52. The swing arm 54 is then pivoted to a second position as shown in solid lines in FIG. 9 and the contents of the liner 14 drained. The second position may be a substantially horizontal position as shown in FIG. 9, or the second position may be any position that allows as much fluid as possible to drain out of the liner 14. After drainage is completed, the swing arm 54 is returned to its first position and the apparatus 10 can be removed from the swing arm 54.

Figure 10:
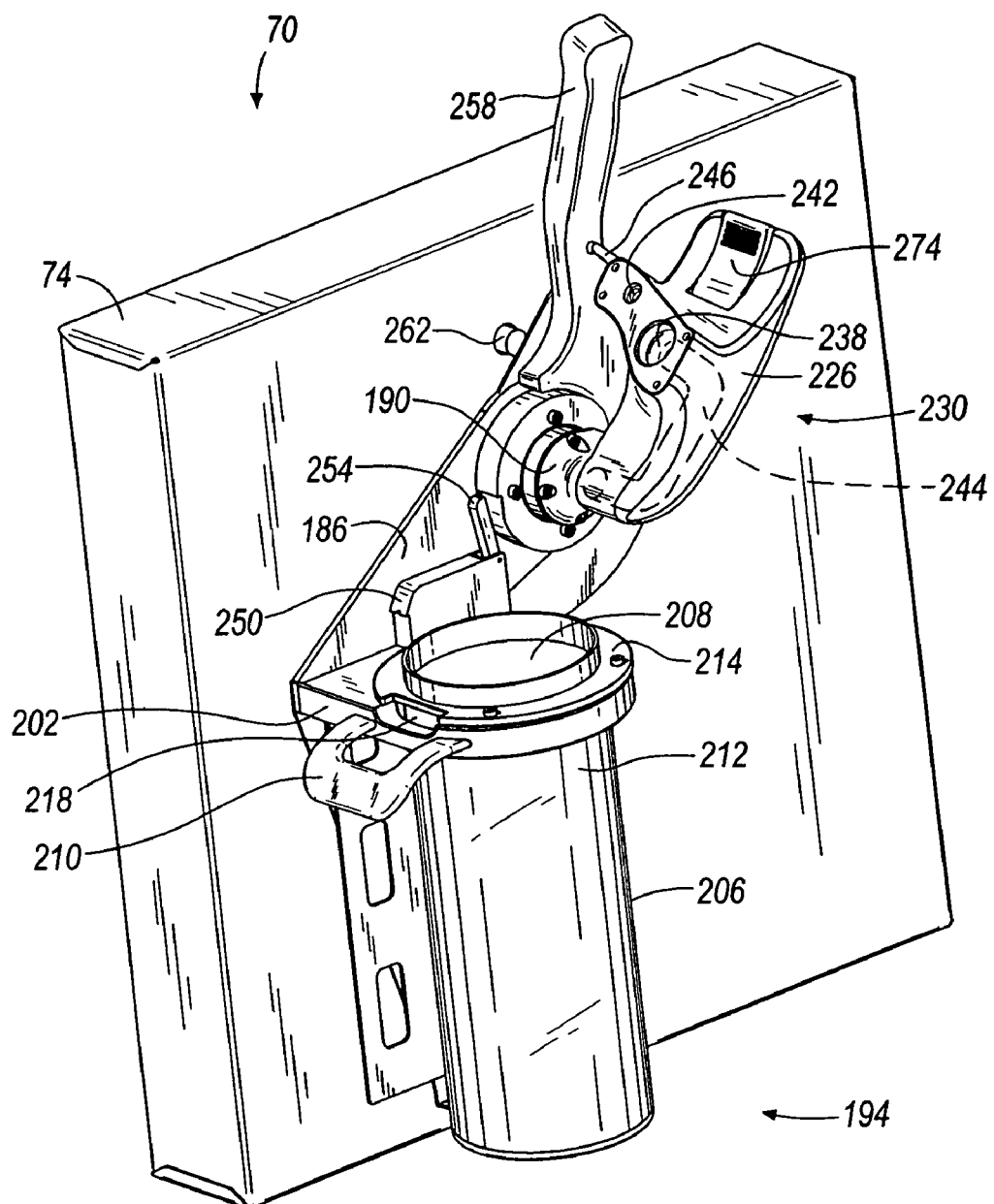
FIG. 10 is a perspective view of an apparatus and a method for draining the liner-type medical suction apparatus.

FIG. 10 illustrates a drainage device 70 that can be used to drain the liner 14. The drainage device 70 can be positioned on the floor (i.e., freestanding) or mounted to a wall with hardware (not shown) suitable to support the device 70 on the wall.

Figure 11:
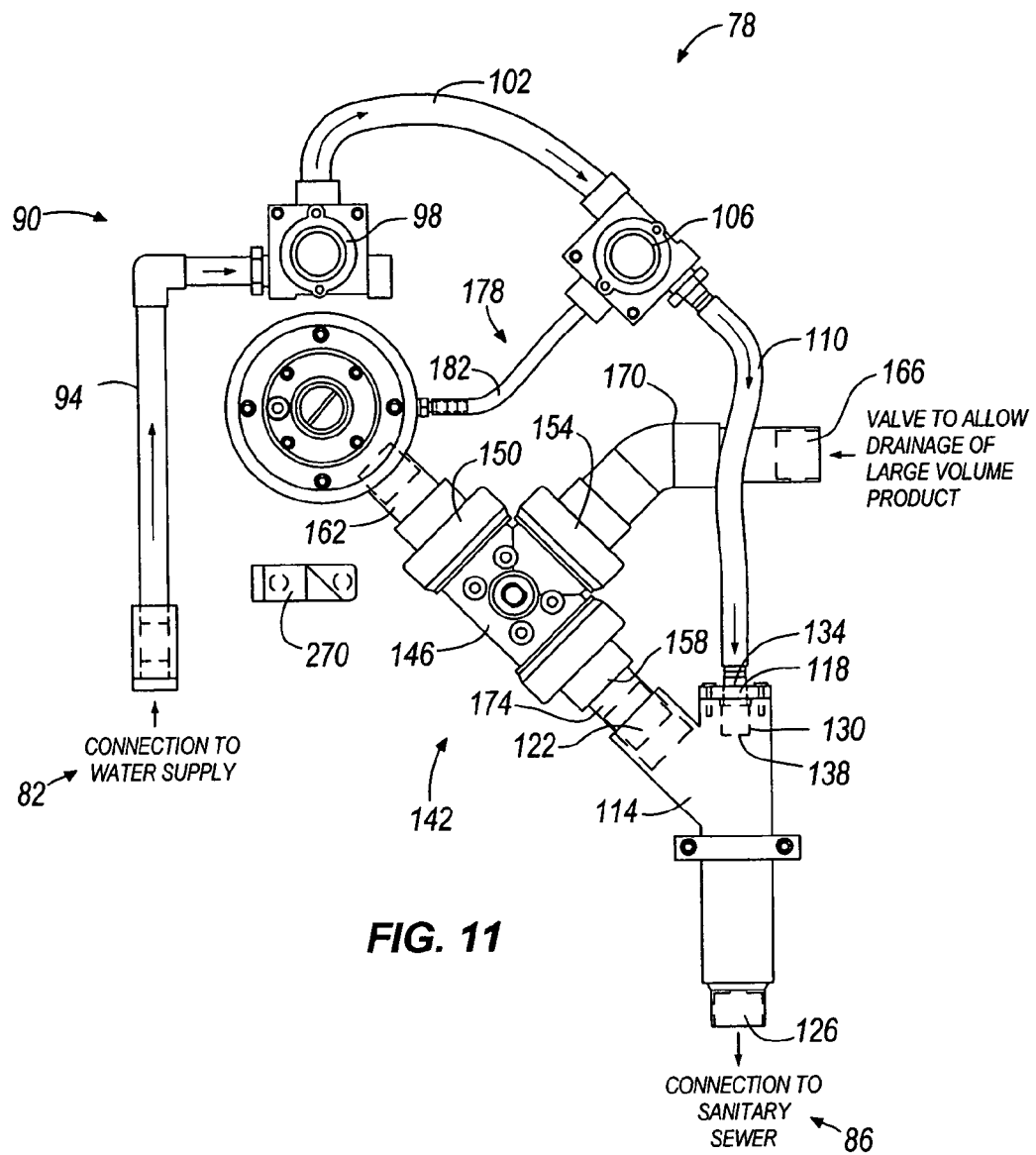
FIG. 11 is a schematic of a plumbing system of the apparatus in FIG. 10.

The drainage device 70 includes a housing 74, which supports a plumbing system 78 (illustrated in FIG. 11). The plumbing system 78 can be supported inside the housing 74, outside the housing 74 or partially inside and outside the housing 74. The plumbing system 78 connects to a water supply 82 and sanitary sewer system 86 as illustrated in FIG. 11.

The plumbing system 78 is not limited to the arrangement illustrated in FIG. 11, but rather any number of plumbing systems, components, and/or assemblies, such as conduits, joints, pipes, valves, and the like, can be combined to implement the plumbing system 78, which is within the scope of the invention. FIG. 11 illustrates only one embodiment of the plumbing system 78 utilized with the drainage device 70.

The plumbing system 78 includes a water supply circuit 90, which connects the water supply 82 to the sanitary sewer system 86. The water supply circuit 90 includes a valve 98 and a conduit 94 (or a plurality of conduits that are connectable to form conduit 94) connectable between the water supply 82 and the valve 98. The water supply circuit 90 also includes a spray nozzle valve 106 and a conduit 102 (or a plurality of conduits that are connectable to form conduit 102) connectable between the valve 98 and the valve 106. The water supply circuit 90 further includes a suction generator, such as a jet pump 114 and a conduit 110 (or a plurality of conduits that are connectable to form conduit 110) connectable between the valve 106 and the jet pump 114. The jet pump 114 includes a first inlet 118, a second inlet 122, and an outlet 126. The outlet 126 of the jet pump 114 is connectable to the sanitary sewer system 86. The jet pump 114 includes a jet pump nozzle 130, a jet pump inlet 134 and a jet pump outlet 138. The jet pump inlet 134 receives the water supplied by the water supply 82 through the conduits 94, 102, and 110 and valves 98 and 106. The jet pump nozzle 130 generates a high velocity fluid stream and directs the high velocity fluid stream through the jet pump outlet 138, which generates suction at the second inlet 122 of the jet pump 114.

The plumbing system 78 includes a waste flow circuit 142, which connects a drainhead (discussed below) supported on the housing 74 to the sanitary sewer system 86. The waste flow circuit 142 includes a joint conduit 146 having a first inlet 150, a second inlet 154, and an outlet 158. The waste flow circuit 142 also includes a conduit 162 (or a plurality of conduits that are connectable to form conduit 162) connectable to the drainhead (discussed below) and the first inlet 150 of the joint conduit 146. The waste flow circuit 142 further includes a drainage valve 166 and a conduit 170 (or a plurality of conduits that are connectable to form conduit 170) connectable to the valve 166 and the second inlet 154 of the joint conduit 146. The valve 166 can be used to drain larger volumes and/or amounts of product/waste to the sanitary sewer system 86. The waste flow circuit 142 also includes a conduit 174 (or a plurality of conduits that are connectable to form conduit 174) connectable to the outlet 158 of the conduit 146 and the second inlet 122 of the jet pump 114.

The plumbing system 78 includes a water spray circuit 178, which connects the water supply 82 to the drainhead (discussed below). The water spray circuit 178 includes a conduit 182 connectable to the valve 106 and the drainhead (discussed below) to allow the flow of water to the interior of the liner 14.

Referring back to FIG. 10, the housing 74 includes a member 262, which when contacted, activates and/or opens the water valve 98 to start the flow of water from the water supply 82 through the water supply circuit 90. The housing 74 also includes a member 266 (illustrated in FIG. 13) to activate the valve 106 to allow the flow of water to enter the water spray circuit 178, through the drainhead (discussed below), and into the interior of the liner 14.

The housing 74 supports a swingarm 186 as illustrated in FIG. 10. The swingarm 186 is pivotably mounted to the housing 74 through a shaft (not shown) at pivot point 190. The swingarm 186 is pivotably movable between a first position 194 and a second position 198 (illustrated in FIG. 14). In some embodiments of the invention, the second position 198 is in the range of about 90 degrees to about 180 degrees, and more particularly in the range of about 100 degrees to about 140 degrees, and most preferably about 135 degrees, from the first position 194. The swingarm 186 pivots in a clockwise direction when moved between the first position 194 and the second position 198. Likewise, the swingarm 186 rotates in a counter-clockwise direction when moved between the second position 198 and the first position 194. However, movement of the swingarm 186 between positions 194 and 198 can be modified to pivot in varying directions.

The swingarm 186 includes a support member, such as a canister bracket 202, which supports a rigid walled container, such as annular canister 206. The canister includes an opening 208 and an interior 212 adapted to receive the liner-type medical suction apparatus 10. The canister bracket 202 can include a canister handle 210. The canister bracket 202 supports a flange 214. The flange 214 is mounted to the canister bracket 202 and supports the liner-type medical suction apparatus 10 when it is positioned in the canister 206.

The canister bracket 202 includes an alignment member, such as a notch 218 to align a handle 222 (illustrated in FIG. 13) on the liner-type medical suction apparatus 10 to properly position the liner-type medical suction apparatus 10. Specifically, the notch 218 aligns the cover 12 relative to the drainhead (discussed below). The cover 12 interengages with the flange 214 to create an airtight seal within the canister 206.

The swingarm 186 supports a drainhead 226. The drainhead 226 is preferably pivotably movable between a first position 230 and a second position 234 (illustrated in FIG. 13). In some embodiments of the invention, the second position 234 is in the range of about 90 degrees to about 180 degrees, and more particularly in the range of about 100 degrees to about 140 degrees, and most preferably about 135 degrees, from the first position 230. The drainhead 226 pivots in a counter-clockwise direction when moved between the first position 230 and the second position 234. Likewise, the drainhead 226 rotates in a clockwise direction when moved between the second position 234 and the first position 230. However, movement of the drainhead 226 can be modified to pivot in any direction.

As illustrated in FIG. 10, the drainhead 226 includes a drainage port 238 and a spray port 242. The drainage port 238 interengages with the open port 24 on the cover 12 of the liner-type medical suction apparatus 10 and the spray port 242 interengages with the patient port 18 on the cover 12 when the drainhead 226 is in the second position 234 (shown in FIG. 13). The drainhead 226 can include additional ports to interengage with other ports on the cover 12. The drainhead 226 includes a passageway 244 adapted to be in fluid communication with the open port 24 on the cover 12 and the conduit 162.

The drainhead 226 includes a latch 246 that engages a swingarm lock 250, which is supported on the swingarm 186. The swingarm 186 also includes an interlock 254 that is released when the latch 246 engages the swingarm lock 250. The swingarm interlock 254 is positioned in such a manner to prevent the swingarm 186 from rotating without the drainhead 226 properly secured to the cover 12 of the liner-type medical suction apparatus 10. With the interlock 254 released, the swingarm 186 is free to be moved.

The drainhead 226 includes a lever 274, which, when activated, releases the drainhead latch 246 from the swingarm lock 250 so the drainhead 226 can be moved from the second position 234 to the first position 230.

The swingarm 186 includes a handle 258 as illustrated in FIG. 10. The handle 258 is engaged by an operator of the drainage device 70 to rotate the swingarm 186 and liner-type medical suction apparatus 10 to dispose of the contents in the liner 14. As the swingarm 186 is rotated, the swingarm 186 contacts the member 262, which activates and/or opens the water valve 98 and the jet pump 130 to start the flow of water from the water supply 82 through the water supply circuit 90.

The drainage device 70 operates to drain the contents of the liner 14 in a manner in which there is minimal and preferably no contact with the liner contents. An operator positions the liner-type medical suction apparatus 10 (in need of emptying or draining) in the canister 206, aligns the handle 222 with the notch 218 on the canister bracket 202, and inserts or presses the cover 12 onto the rim of the flange 214 to create an airtight seal within the canister 206. The airtight seal keeps the liner 14 expanded during the drainage process to allow for more complete drainage of the liner 14.

Figure 12:
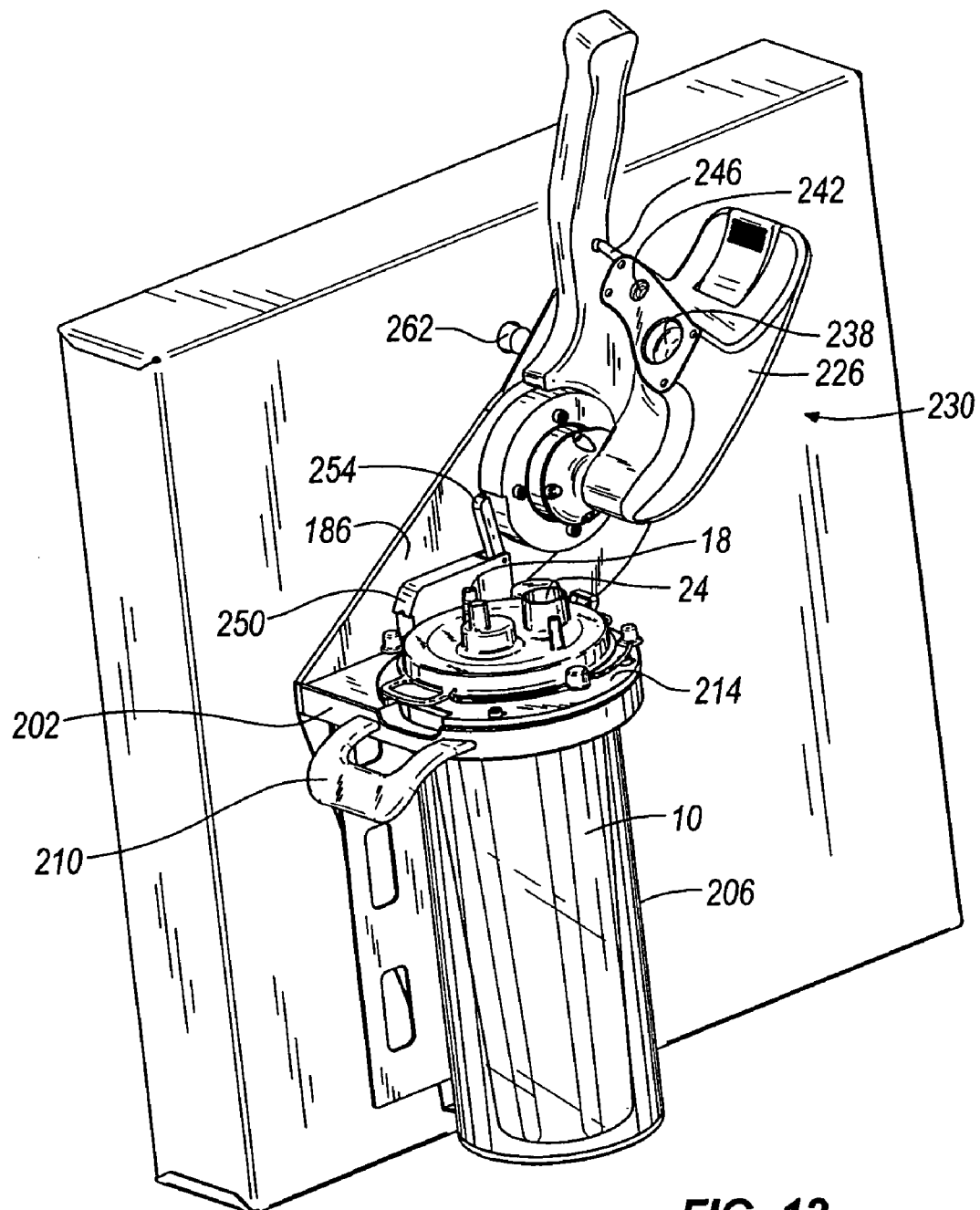
FIG. 12 is a perspective view of the apparatus in FIG. 10 including the liner-type medical suction apparatus.

The operator removes a cap(s) or like devices (not shown) from the patient port 18 and the open port 24. Next, the operator moves the drainhead 226 from its first position 230 to its second position 234 (illustrated in FIGS. 12-13) such that the latch 246 engages the swingarm lock 250 to release the swingarm interlock 254.

Figure 13:
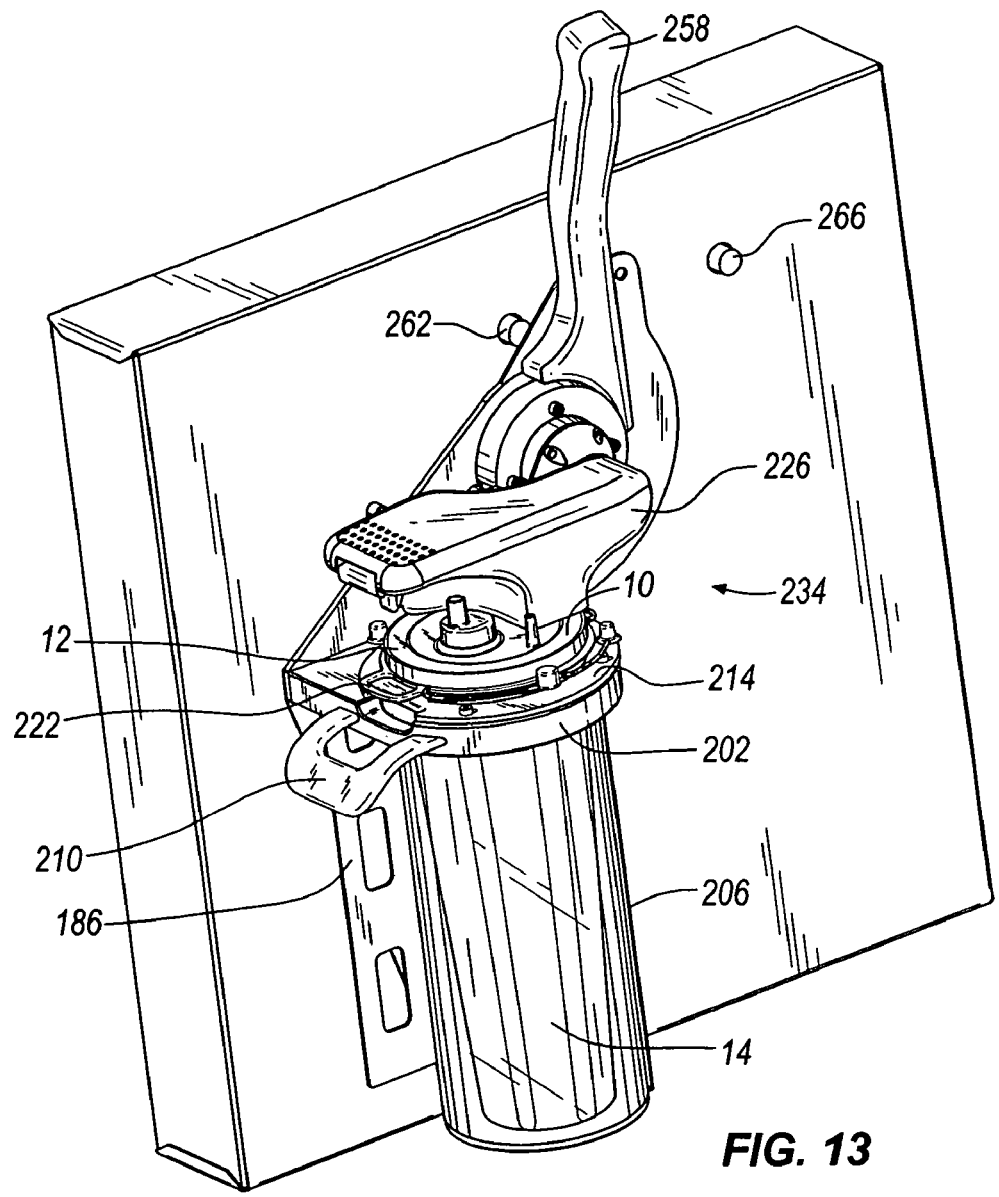
FIG. 13 is a perspective view of the apparatus in FIG. 10.
Figure 14:
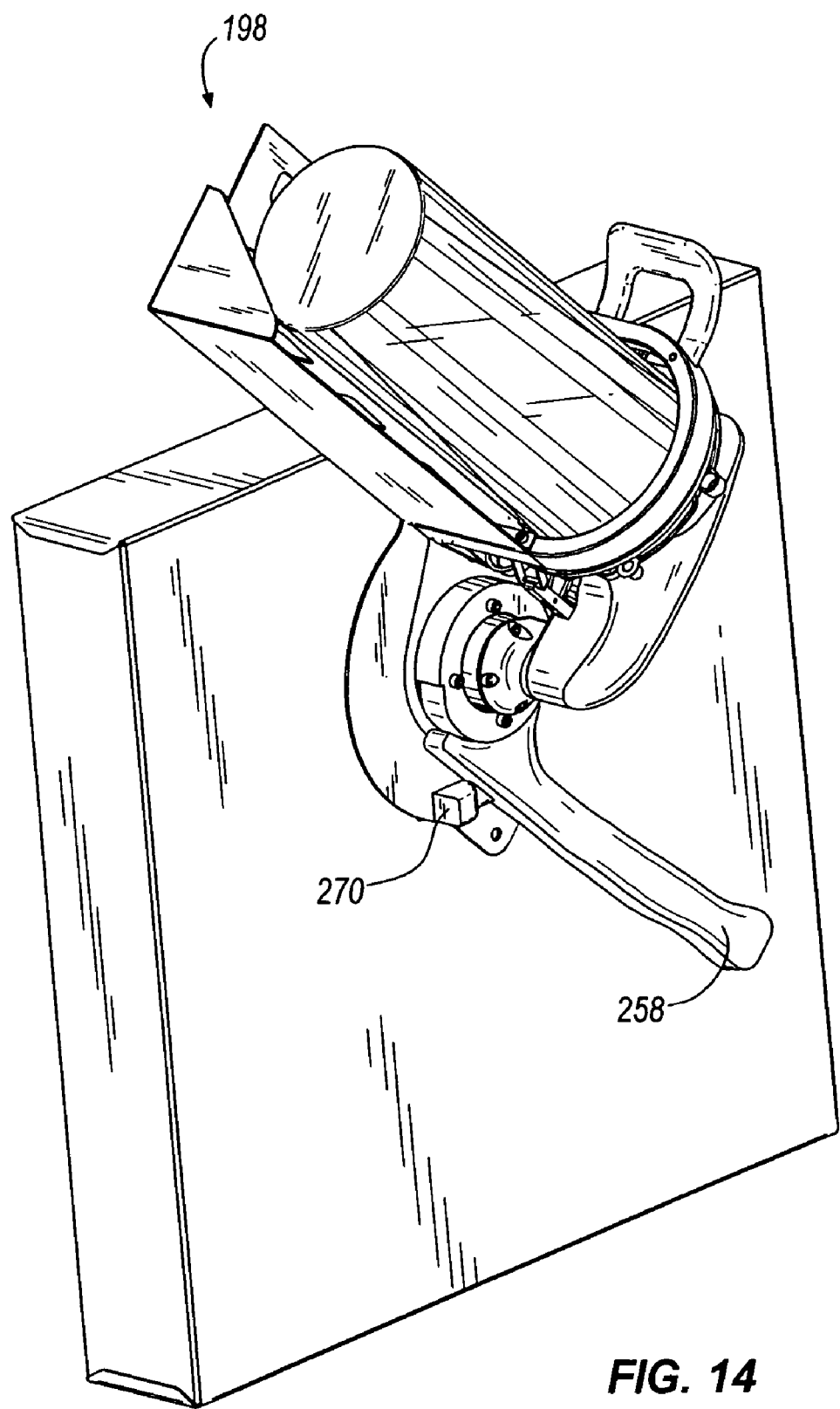
FIG. 14 is a perspective view of the apparatus in FIG. 10.

The operator engages the handle 258, the canister handle 210, and/or the canister 206 to move the swingarm 186 from the first position 194 to the second position 198 (illustrated in FIGS. 13-14). As the swingarm 186 is moved (and generally before the swingarm reaches the second position 198), the swingarm 186 contacts member 262, which activates and/or opens the valve 98 and the jet pump 114 to start the flow of water from the water supply 82 through the water supply circuit 90. The swingarm 186 is moved clockwise (about 135 degrees) until the handle 258 makes contact with a stop 270 (illustrated in FIG. 14) supported by the housing 74.

The flow of water through the water supply circuit 90 and jet pump nozzle 130 generates suction at the second inlet 122 of the jet pump 114 and in the interior of the liner 14. The suction along with gravity facilitate drainage of the contents of the liner 14. The contents travel through the open port 24, through the passageway 244 in the drainhead 226 to the waste flow circuit 142 and to the sanitary sewer system 86.

After drainage of the liner 14 is completed, the operator can optionally activate the member 266 (illustrated in FIG. 13), which allows water to enter the water spray circuit 178, through the drainhead 226, spray port 242, patient port 18, and into the interior of the liner 14. The water is sprayed into the liner 14 to clean/rinse the walls of the liner 14 and drained through the open port 24, the passageway 244 in the drainhead 226 to the waste flow circuit 142 and to the sanitary sewer system 86.

After completion, the operator engages the handle 258, the handle 210 and/or the canister 206 to move the swingarm 186 from the second position 198 to the first position 194 (until the swingarm 186 contacts the stop 270). The operator then depresses the lever 274 on the drainhead 226 to release the latch 246, and moves the drainhead 226 from the second position 234 to the first position 230. The operator can remove the liner-type medical suction apparatus 10 from the canister 206 and dispose of it in a red bag medical waste container.

Figure 15:
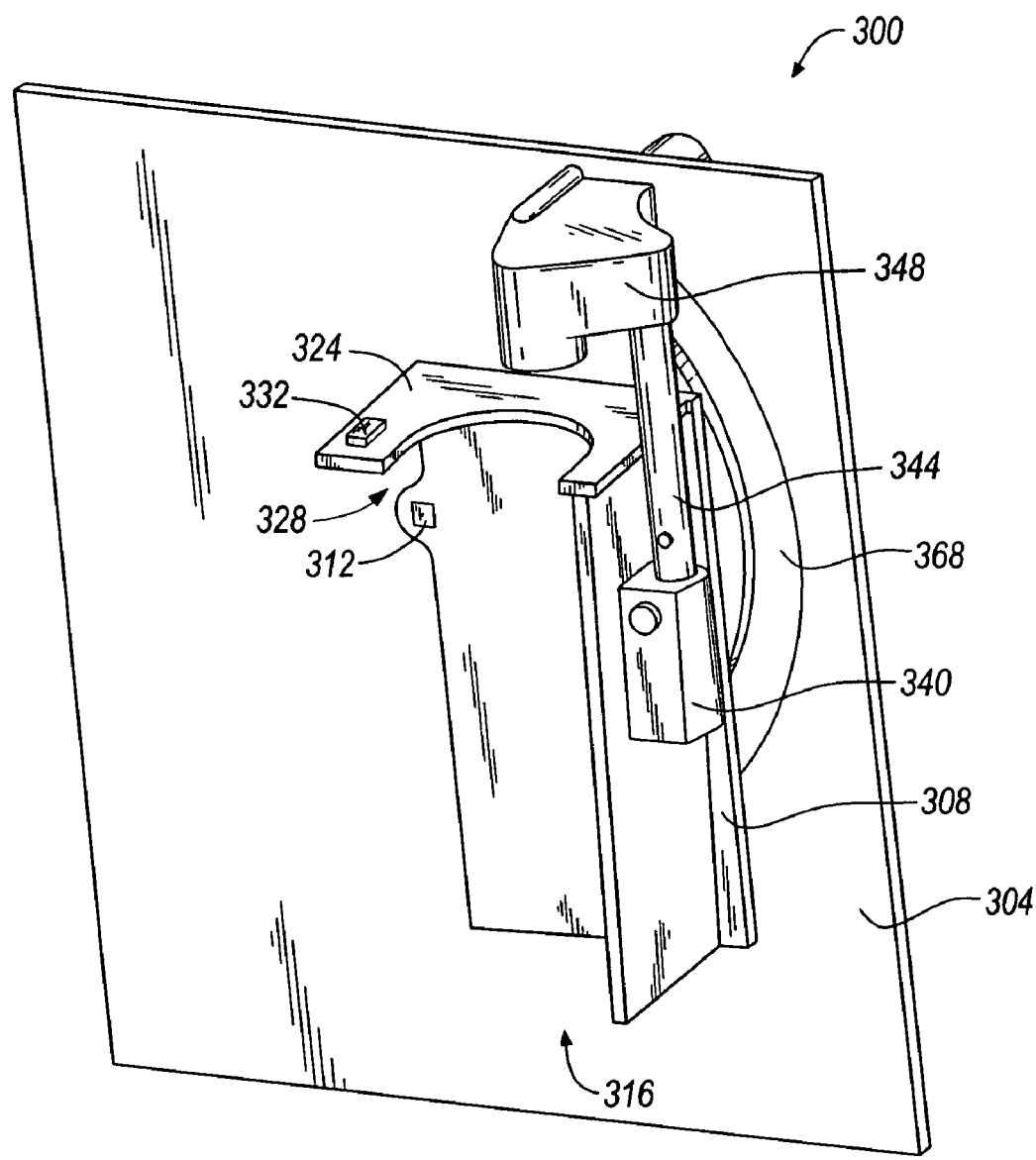
FIG. 15 is a perspective view of an apparatus and a method for draining the liner-type medical suction apparatus.

FIG. 15 illustrates a drainage device 300 that can be used to drain the liner 14. The drainage device 300 can be positioned on the floor (i.e., freestanding) or mounted to a wall with hardware (not shown) suitable to support the device 300 on the wall.

The drainage device 300 includes a housing 304, which supports a swingarm 308 as illustrated in FIG. 15. The swingarm 308 is pivotably mounted to the housing 304 through a shaft (not shown) at pivot point 312 (shown in FIGS. 15 and 18-21). The swingarm 308 is pivotably movable between a first position 316 (illustrated in FIG. 15) and a second position 320 (illustrated in FIG. 20).

In some embodiments of the invention, the second position 320 is in the range of about 90 degrees to about 180 degrees, and more particularly in the range of about 100 degrees to about 140 degrees, and most preferably about 135 degrees, from the first position 316. The swingarm 308 pivots in a clockwise direction when moved between the first position 316 and the second position 320. Likewise, the swingarm 308 rotates in a counter-clockwise direction when moved between the second position 320 and the first position 316. However, movement of the swingarm 308 can be modified to vary in the type and direction of movement.

The swingarm 308 includes a support member, such as a bracket 324, which includes an opening 328. The bracket 324 supports the liner-type medical suction apparatus 10 when positioned in the opening 328 (illustrated in FIG. 16). The bracket 324 can also support a rigid walled container, such as an annular canister (not shown) adapted to support the liner-type medical suction apparatus 10 when positioned in the canister. The bracket 324 includes an alignment member, such as a notch 332 to align a handle 336 (illustrated in FIG. 16) on the cover 12 of the liner-type medical suction apparatus 10 to properly position the cover 12 in the opening 328. The notch 332 aligns the cover 12 relative to a drainhead (discussed below).

Referring to FIG. 15, the swingarm 308 includes a piston module 340, which supports a conduit 344. The conduit 344 supports a drainhead 348 that moves vertically with the conduit 344 to interengage with the cover 12 of the liner-type medical suction apparatus 10 (illustrated in FIG. 20). The piston module 340 can be spring-loaded and biased in an open position.

Figure 17:
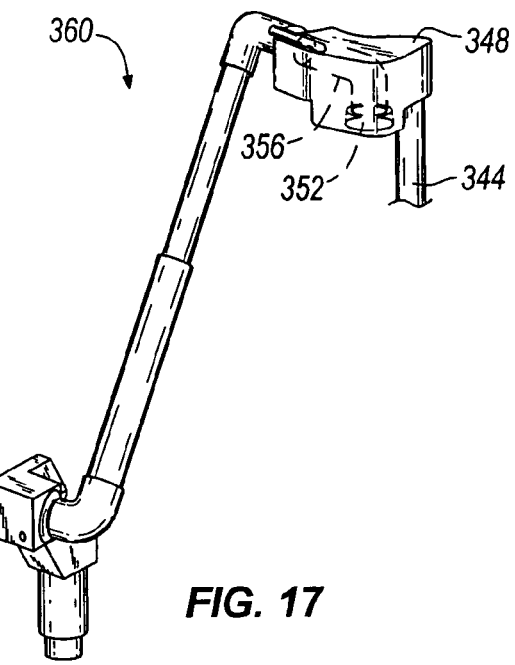
FIG. 17 is a perspective view of a drainhead assembly and a plumbing system of the apparatus in FIG. 15.

As illustrated in FIG. 17, the drainhead 348 includes a drainage port 352 and a passageway 356 in fluid communication with the drainage port 352 and a plumbing system 360. The drainage port 352 in the drainhead 348 interengages with the open port 24 on the cover 12 of the liner-type medical suction apparatus 10 (illustrated in FIG. 20).

Figure 18:
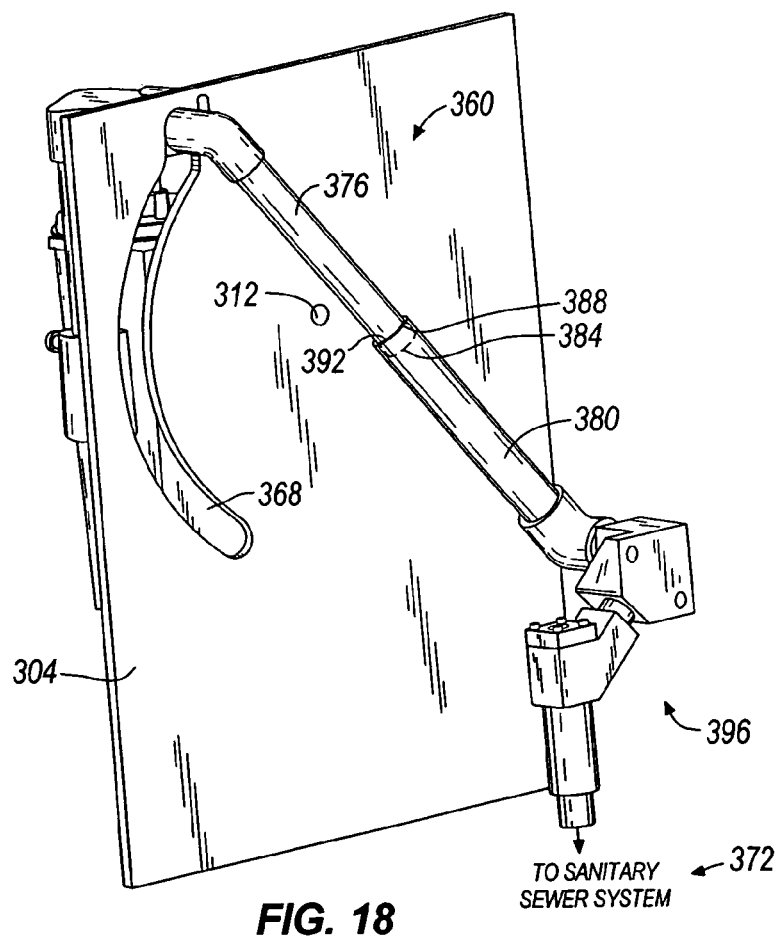
FIG. 18 a back perspective view of the plumbing system of the apparatus in FIG. 15.
Figure 19:
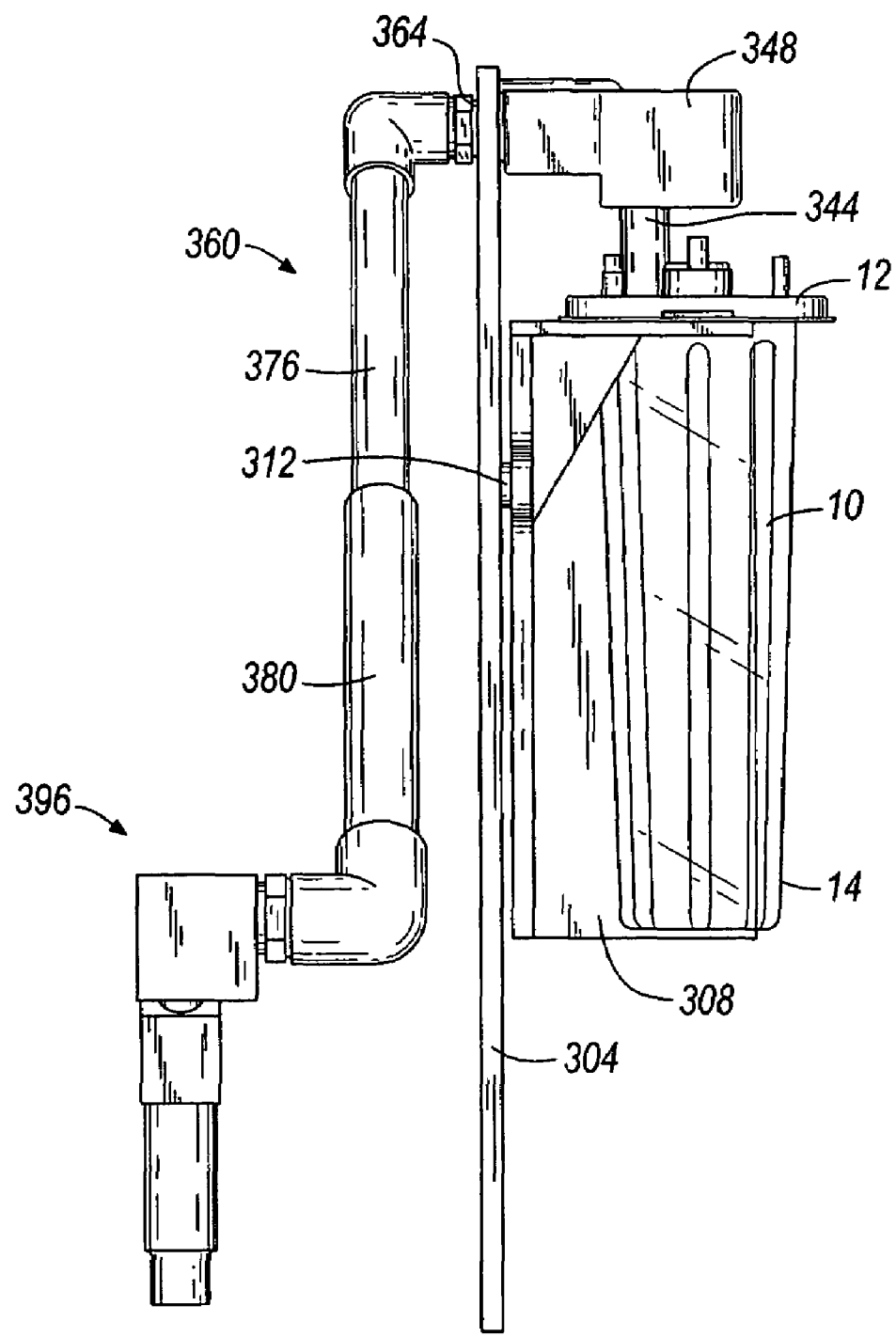
FIG. 19 is a side elevational view of the apparatus in FIG. 15 including the liner-type medical suction apparatus.
Figure 21:
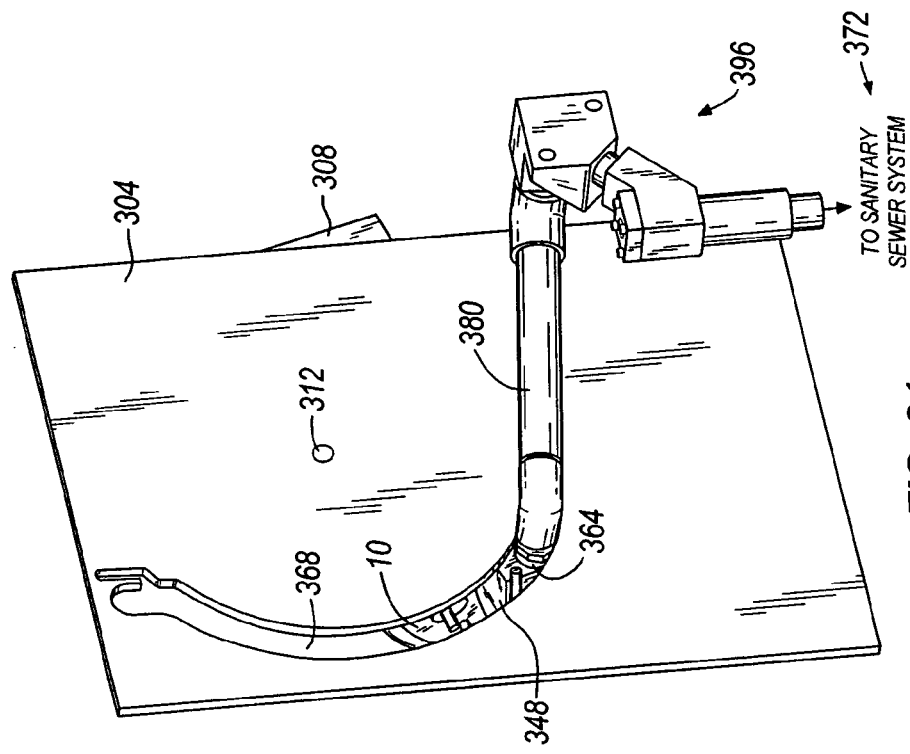
FIG. 21 is a back perspective view of the apparatus in FIG. 15.
Figure 20:
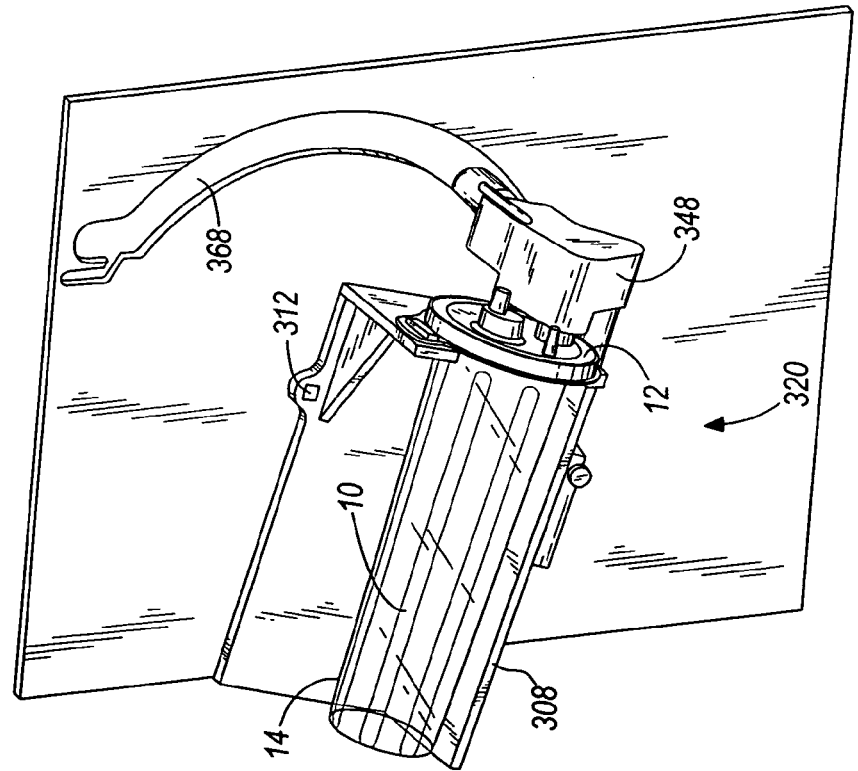
FIG. 20 is a perspective view of the apparatus in FIG. 15.

As best illustrated in FIGS. 19 and 21, the drainhead 348 includes a conduit 364 that is connected to the plumbing system 360. The conduit 364 moves along a guide or pathway 368 (illustrated in FIGS. 15-16, 18 and 20-21) formed in the housing 304 when the swingarm 308 is moved.

Referring to FIGS. 17 and 18, the housing 304 includes the plumbing system 360, which can be supported inside the housing 304, outside the housing 304 or partially inside and outside the housing 304. The plumbing system 360 connects to a sanitary sewer system 372. The plumbing system 360 includes a conduit 376 (or a plurality of conduits that are connectable to form conduit 376) connectable to the conduit 364 and a conduit 380. An end 384 of the conduit 376 is positioned within an end 388 having an opening 392 of the conduit 380 and slides/glides within the opening 392 of the conduit 380. The plumbing system 360 includes a suction generator, such as a jet pump 396 connectable to the conduit 380 and the sanitary sewer system 372.

Figure 16:
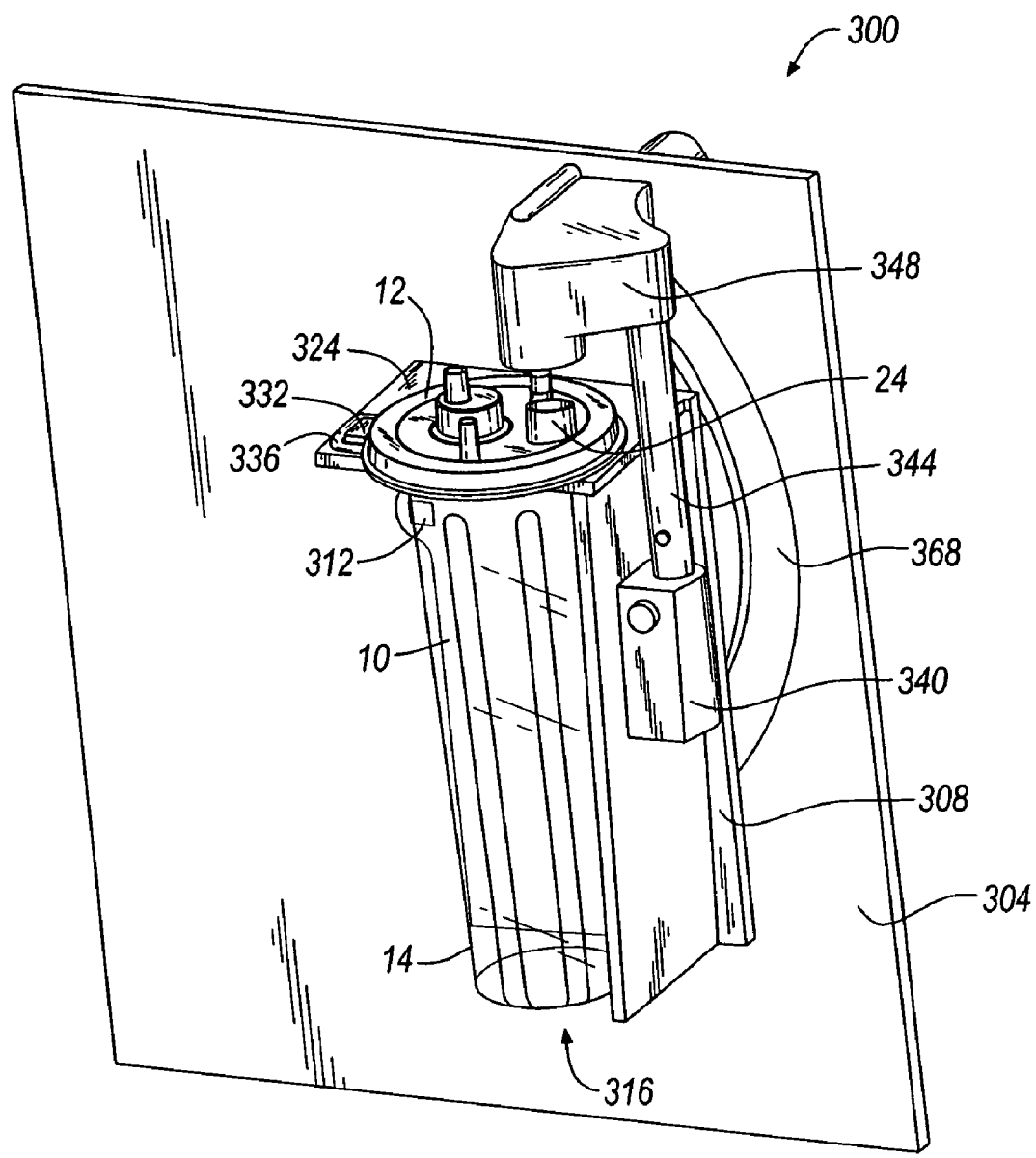
FIG. 16 is a perspective view of the apparatus in FIG. 15 including the liner-type medical suction apparatus.

The drainage device 300 operates to drain the contents of the liner 14 in a manner in which there is minimal and preferably no contact with the liner contents. An operator positions the liner-type medical suction apparatus 10 (in need of emptying or draining) in the opening 328 of the bracket 324 and aligns the handle 336 with the notch 332 on the bracket 324 as illustrated in FIG. 16.

After the liner-type medical suction apparatus 10 is in position, the operator removes a cap(s) or like devices (not shown) from the open port 24 and activates the piston module 340, which automatically moves the drainhead to contact the cover 12. Alternatively, the operator manually moves the drainhead 348 into contact with the cover 12. As the drainhead 348 moves vertically downward onto the cover 12, the conduit 364 travels in the pathway 368 for proper alignment with the open port 24 on the cover.

When the drainhead 348 is properly seated on the cover 12 of the liner 14, a release lever (not shown) and the jet pump 396 are activated (not necessarily, but could be a simultaneous activation), the swingarm 308 moves and the conduit 364 travels in the pathway 368 such that the liner-type medical suction apparatus 10 is transported from the first position 316 to the second position 320 as determined by the pathway 368 (illustrated in FIGS. 16, 18-21). The operator does not need to manually move the swingarm 308, rather the swingarm 308 moves into the second position 320 under gravity and the weight of the contents in the liner 14. In some embodiments, the operator can manually move the swingarm 308 into the second position 320 as guided by the pathway 368. The swingarm 308 remains in the second position 320 by a lock mechanism (not shown).

As illustrated in FIGS. 18 and 21, as the swingarm 308 moves between the first position 316 and the second position 320, the conduit 376 slides into the conduit 380. With the swingarm 308 and the liner-type medical suction apparatus 10 in the second position 320, the contents in the liner 14 are drained by gravity and suctioned by the jet pump 396 through the drainage port 352, the passageway 356 in the drainhead 348, conduits 364, 376, and 380 to the sanitary sewer system 372. The swingarm 308 remains in the second position 320 until drainage of the liner 14 is completed.

After drainage of the liner 14 is completed, the operator disengages the lock mechanism (not shown), and the swingarm 308 and liner-type medical suction apparatus 10 are returned to the first position 316 by the operator. The operator activates the piston module 340, which automatically moves the drainhead 348 away from the cover 12. In some embodiments, the operator manually moves the drainhead 348 away from the cover 12. The operator can then remove the liner-type medical suction apparatus 10 from the bracket 324 and dispose of it in a red bag medical waste container.

FIGS. 22-25 illustrate another drainage device 400 that can be used to drain the liner 14. The drainage device 400 can be positioned on the floor (i.e., freestanding) or mounted to a wall with hardware (not shown) suitable to support the device 400 on the wall.

Figure 22:
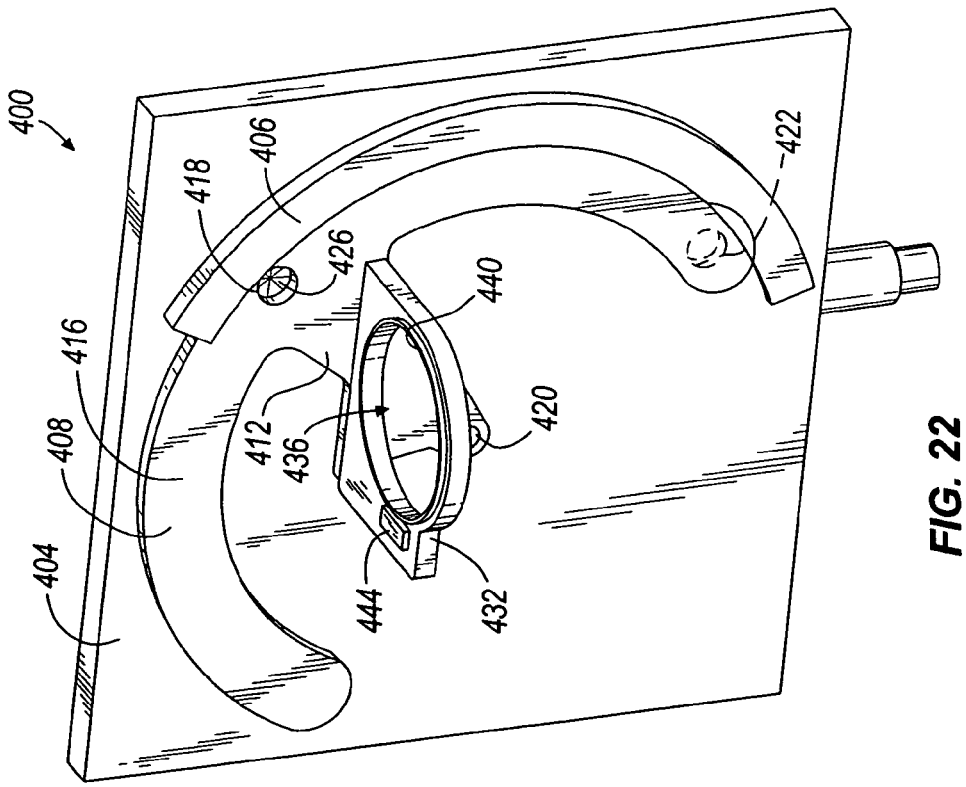
FIG. 22 is a perspective view of an apparatus and a method for draining the liner-type medical suction apparatus.

The drainage device 400 includes a housing 404, which supports a channel 406. The channel 406 guides and supports a swingarm 408 as illustrated in FIG. 22. The swingarm 408 can be a plate-like device with a central portion 412 and a C-shaped portion 416. The C-shaped portion 416 includes an opening 418, which aligns with an opening 422 in the housing 404. The opening 418 includes a closure device 426, such as a dynamic seal, a valve, flap, and like devices. The closure device 426 prevents the contents of the liner 14 from leaking out of the drainhead (discussed below) until the opening 418 in the swingarm 408 is aligned with the opening 422 in the housing 404. Alternatively, the closure device 426 can be positioned in the opening 422 of the housing 404. The central portion 412 of the swingarm 408 is pivotably mounted to the housing 404 through a shaft (not shown) at pivot point 420 (shown in FIGS. 22-25). The swingarm 408 is pivotably movable between a first position 424 (illustrated in FIG. 23) and a second position 428 (illustrated in FIG. 25).

In some embodiments of the invention, the second position 428 is in the range of about 90 degrees to about 180 degrees, and more particularly in the range of about 100 degrees to about 140 degrees, and most preferably about 135 degrees, from the first position 424. The swingarm 408 pivots in a clockwise direction when moved from the first position 424 to the second position 428. Likewise, the swingarm 408 rotates in a counter-clockwise direction when moved from the second position 428 to the first position 424. However, movement of the swingarm 408 can vary in type of motion and direction.

The swingarm 408 includes a support member, such as a bracket 432 having an opening 436. The bracket 432 supports a flange 440, which is mounted to the bracket 432 and supports the liner-type medical suction apparatus 10 when it is positioned in the opening 436. The bracket 432 includes an alignment member, such as a notch 444, to properly position the cover 12 in the opening 436. The notch 444 aligns the cover 12 relative to a drainhead (discussed below).

In some embodiments, the bracket 432 can support a rigid walled container, such as an annular canister 448, adapted to support the liner 14 when positioned in the canister 448. The cover 12 interengages with the flange 440 to create an airtight seal within the canister 448.

Figure 23:
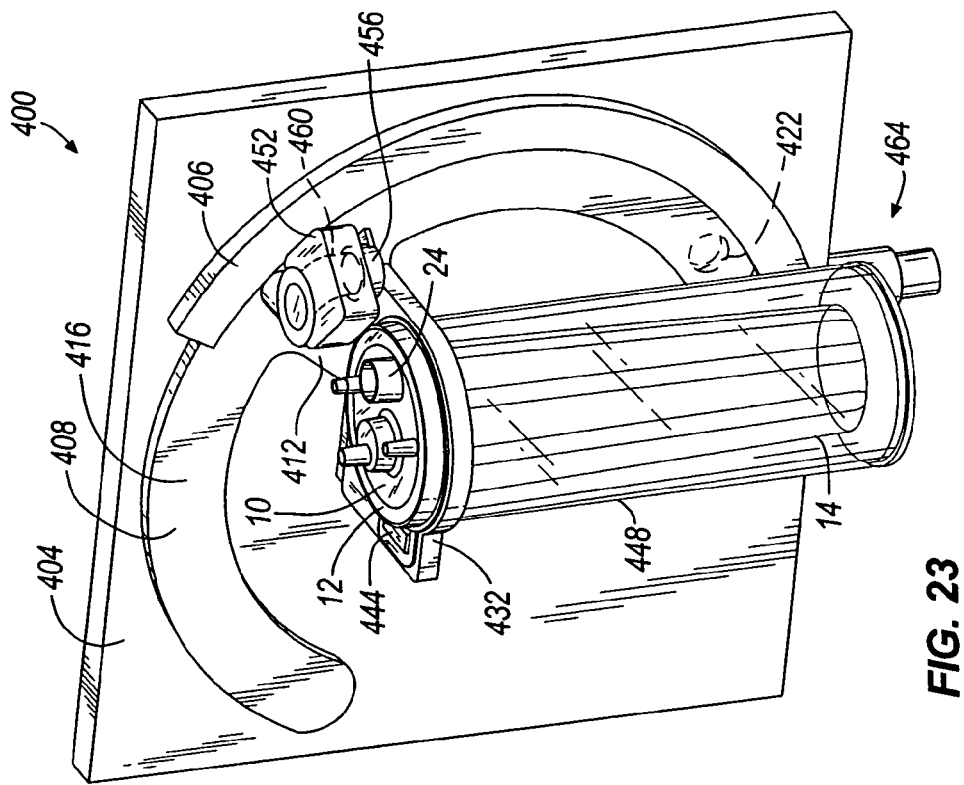
FIG. 23 is a perspective view of the apparatus in FIG. 22 including the liner-type medical suction apparatus.

As illustrated in FIG. 23, the drainage device includes a drainhead 452, which includes a drainage port 456 and a passageway 460 in fluid communication with the drainage port 456 and the opening 418 in the swingarm 408. The drainage port 456 in the drainhead 452 interengages with the open port 24 on the cover 12 (illustrated in FIG. 24). The drainhead 452 can pivot onto the open port 24. The drainhead 452 can also be configured to be spring-biased in the open position and manually moved onto the open port 24. The drainhead 452 can be further configured to align with the open port 24 in any suitable manner.

Figure 24:
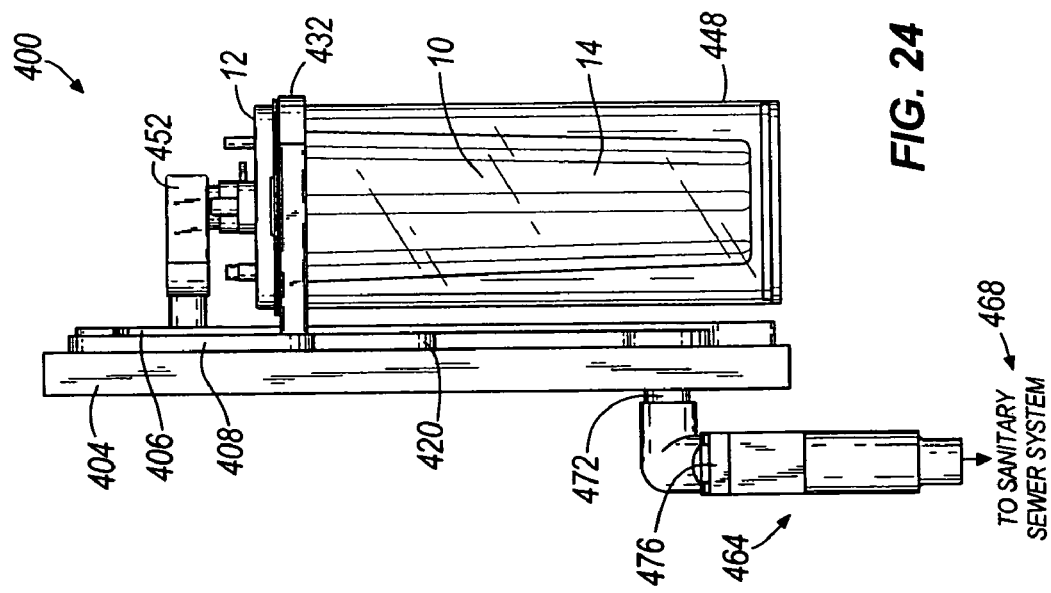
FIG. 24 is a side elevational view of the apparatus in FIG. 22 including the liner-type medical suction apparatus.

Referring to FIG. 24, the housing 404 includes a plumbing system 464, which can be supported inside the housing 404, outside the housing 404 or partially inside and outside the housing 404. The plumbing system 464 connects to a sanitary sewer system 468. The plumbing system 464 includes a conduit 472 (or a plurality of conduits that are connectable to form conduit 472) in fluid communication with the opening 422 in the housing 404. The plumbing system 464 also includes a suction generator, such as a jet pump 476 connectable to the conduit 472 and the sanitary sewer system 468 (through additional conduits).

The drainage device 400 operates to drain the contents of the liner 14 in a manner in which there is minimal and preferably no contact with the liner contents. An operator positions the liner-type medical suction apparatus 10 (in need of emptying or draining) in the bracket 432 and aligns the cover 12 with the notch 444 on the bracket 432 as illustrated in FIG. 23.

After the liner-type medical suction apparatus 10 is in position, the operator removes a cap(s) or like devices (not shown) from the open port 24 on the cover 12 and activates the drainhead 452 to automatically move onto the cover 12. In some embodiments, the operator manually moves the drainhead 452 onto the cover 12. The drainhead 452 moves vertically downward and/or swivels onto the cover 12 of the liner 14 to align the drainage port 456 and be in fluid communication with the open port 24 on the cover 12.

Figure 25:
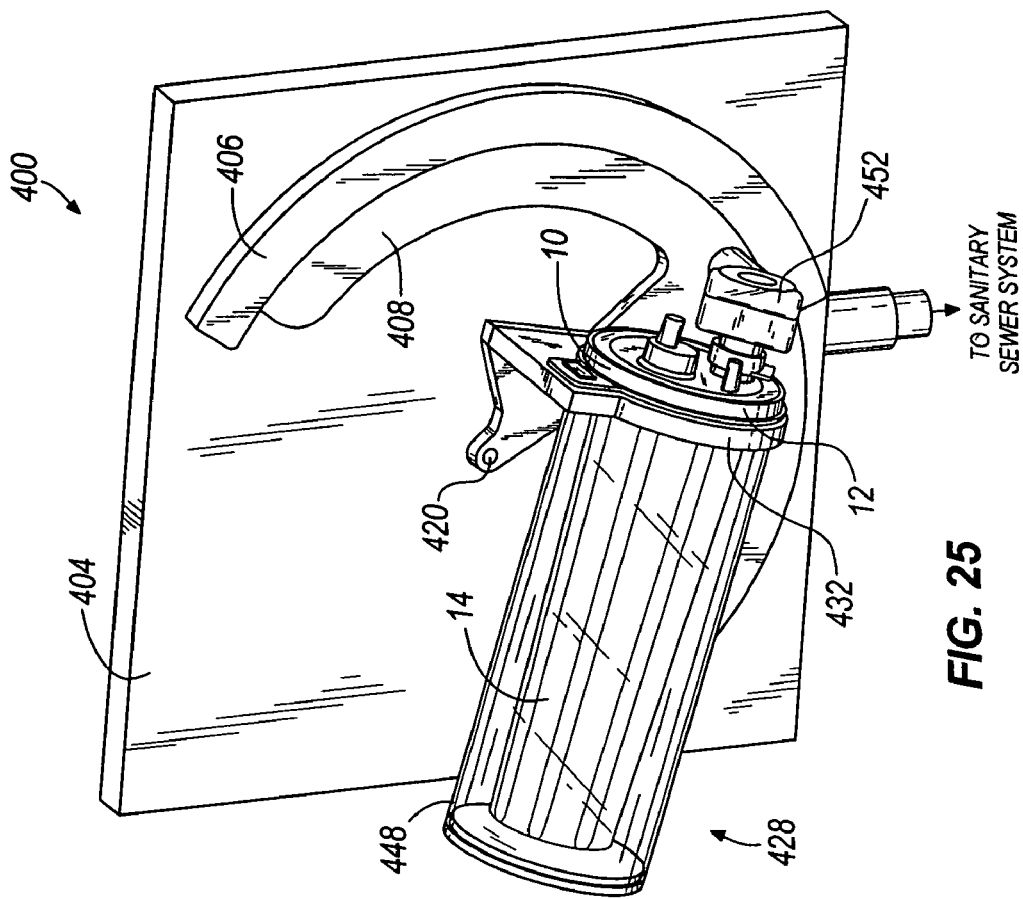
FIG. 25 is a perspective view of the apparatus in FIG. 22

When the drainhead 452 is properly seated on the cover 12, a release lever (not shown) and the jet pump 476 are activated (not necessarily, but could be a simultaneous activation), the swingarm 408 travels in a clockwise path such that the liner-type medical suction apparatus 10 is transported between the first position 424 and the second position 428 (illustrated in FIGS. 23 and 25). The operator does not need to manually move the swingarm 408, rather the swingarm 408 moves into the second position 428 under gravity and the weight of the contents in the liner 14. In some embodiments, the operator can manually move the swingarm 408 into the second position 428. The swingarm 308 remains in the second position 320 by a lock mechanism (not shown).

With the swingarm 408 and the liner-type medical suction apparatus 10 in the second position 428, the contents in the liner 14 are drained by gravity and suctioned by the jet pump 476 through the drainage port 456, the passageway 460 in the drainhead 452, openings 418 and 422, conduit 472 to the sanitary sewer system 468. The swingarm 408 remains in the second position 428 until drainage of the liner 14 is completed.

After drainage of the liner 14 is completed, the operator disengages the lock mechanism (not shown), and the swingarm 408 and liner 14 are returned to the first position 424. The operator activates the drainhead 452, which automatically moves the drainhead 452 away from the cover 12. In some embodiments, the operator manually moves the drainhead 452 away from the cover 12. The operator can then remove the liner-type medical suction apparatus 10 from the bracket 432 and/or canister 448 and dispose of the liner-type medical suction apparatus 10 into a red bag medical waste container.

While the present invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit or scope of applicant's general inventive concept.

Various features and advantages of the invention are set forth in the following claims.

What is claimed:

1. A medical device for draining a liner-type suction canister having a cover and a liner coupled to the cover, the cover having therein a port, the liner containing fluid to be drained, the device comprising:
    a housing in communication with a sanitary sewer line;
    a swingarm coupled to the housing;
    a support member connected to the swingarm for supporting the liner-type suction canister, the swingarm adapted to move the liner-type suction canister between a first position and a second position;
    a drainhead having a passageway therein, the drainhead coupled to the swingarm and moveable between a first position not engageable with the liner-type suction canister and a second position engageable with the liner-type suction canister, and in its second position, the passageway being adapted to be in fluid communication with the port in the cover of the liner-type suction canister; and
    a suction source in communication with the passageway and adapted to drain the fluid contained in the liner-type suction canister from the liner through the drainhead to the sanitary sewer.

2. The medical device of claim 1 wherein when the drainhead is in its first position, the swingarm is unable to move.

3. The medical device of claim 2 wherein the swingarm includes an interlock and wherein when the drainhead is in its first position, the swingarm is unable to move due to the interlock.

4. The medical device of claim 1 wherein the support member includes an alignment member to align the liner-type suction canister relative to the drainhead.

5. The medical device of claim 4 wherein the alignment member is a finger notch that interengages with a cover of the liner-type suction canister.

6. The medical device of claim 1 wherein the suction source is activated when the swingarm is in its second position.

7. The medical device of claim 1 wherein the support member includes a rigid walled container into which a liner-type suction canister is positionable.

8. The medical device of claim 7 wherein when the drainhead is in its second position, an air tight seal is creatable between the cover of the liner-type suction canister and the container.

9. The medical device of claim 1 wherein the swingarm rotates about an axis at least ninety degrees and no more than 180 degrees between its first and second positions.

10. The medical device of claim 1 wherein the drainhead includes a latch, wherein when the drainhead is in its second position, the latch engages the swingarm to positionally fix the drainhead relative to the swingarm.

11. The medical device of claim 10 wherein the swingarm includes a lock, and wherein the latch engages the lock to fix positionally the drainhead relative to the swingarm.

12. The medical device of claim 1 wherein the swingarm includes a handle to enable rotation of the swingarm.

13. The medical device of claim 1 wherein the suction source includes a jet pump.

14. A medical device for draining the fluid contained in a liner-type suction canister, the device comprising:
    a swingarm having thereon a support member adapted to support the liner-type suction canister, the swingarm moveable between a first and a second position; and
    a drainhead pivotable with respect to the swingarm, the drainhead having a passageway therein, the drainhead moveable between a first and a second position, the drainhead adapted to engage the liner-type suction canister to enable fluid communication between the passageway and the fluid contained in the liner-type suction canister when the drainhead is in the second position.

15. The medical device of claim 14 wherein the passageway is in fluid communication with a sanitary sewer, and wherein fluid flows from the passageway to the sanitary sewer.

16. The medical device of claim 14 and further comprising a suction source in communication with the passageway for draining fluid contained in the liner-type suction canister.

17. A medical device for draining fluid contained in a liner-type suction canister having a cover, the device comprising:
    a housing; and
    a swingarm coupled to the housing, the swingarm adapted to move the liner-type suction canister between a first position and a second position, the swingarm including a drainhead having therein a passageway, the drainhead adapted to engage the cover of the liner-type suction canister to permit fluid to drain from the liner-type suction canister through the drainhead to the housing.

18. A method for draining a liner-type suction canister filled with fluid, the method comprising:
    placing the liner-type suction canister on a swingarm of a drainage device;
    coupling together a drainhead on the drainage device and the liner-type suction canister;
    rotating the swingarm and the liner-type suction canister; and
    activating a suction source to drain the fluid from the liner-type suction canister through the drainhead.

19. A method for draining a liner-type suction canister filled with fluid, the method comprising:
    placing the liner-type suction canister on a swingarm of a drainage device;
    connecting a drainhead on the drainage device with the liner-type suction canister so as to establish fluid communication between the drainhead and a port on the liner-type suction canister;
    rotating the swingarm to move the liner-type suction canister; and
    activating a suction source to drain the fluid from the liner-type suction canister through the drainhead.

20. A method for draining a liner-type suction canister filled with fluid, the method comprising:
    placing the liner-type suction canister on a swingarm of a drainage device when the swingarm is in a first position;
    preventing movement of the swingarm;

moving a drainhead on the drainage device from a first position to a second position in fluid communication with a port on the liner-type suction canister;

securing the drainhead in the second position;

enabling movement of the swingarm;

rotating the swingarm from its first position to a second position; and activating a suction source to drain the fluid from the liner-type suction canister, through the drainhead, and to a sanitary sewer.

21. The method of claim 20 and further including the step of orienting the liner-type suction canister with respect to the drainage device.

* * * * *

UNITED STATES PATENT AND TRADEMARK OFFICE
CERTIFICATE OF CORRECTION

| | |
|---|---|
| PATENT NO. | : 7,674,248 B2 |
| APPLICATION NO. | : 10/752652 |
| DATED | : March 9, 2010 |
| INVENTOR(S) | : Barry G. Anderson and Joseph M. Hand |

It is certified that error appears in the above-identified patent and that said Letters Patent is hereby corrected as shown below:

On the Title Page of the patent at (63), add -- Continuation of application No. 09/819,243, filed on March 28, 2001, now U.S. Patent No. 6,626,877 --

On the Title Page of the patent, add -- (60) Provisional application no. 60/192,751 filed on March 28, 2000 --

Signed and Sealed this

Eighth Day of June, 2010

David J. Kappos
*Director of the United States Patent and Trademark Office*